United States Patent
Sawaya

(10) Patent No.: US 11,667,951 B2
(45) Date of Patent: Jun. 6, 2023

(54) CONCEALING INFORMATION PRESENT WITHIN NUCLEIC ACIDS

(71) Applicant: GENEINFOSEC, INC., Boulder, CO (US)

(72) Inventor: Sterling Sawaya, Boulder, CO (US)

(73) Assignee: GENEINFOSEC, INC., Boulder, CO (US)

( * ) Notice: Subject to any disclaimer, the term of this patent is extended or adjusted under 35 U.S.C. 154(b) by 215 days.

(21) Appl. No.: 16/344,004

(22) PCT Filed: Oct. 24, 2017

(86) PCT No.: PCT/US2017/058076
§ 371 (c)(1),
(2) Date: Apr. 22, 2019

(87) PCT Pub. No.: WO2018/081113
PCT Pub. Date: May 3, 2018

(65) Prior Publication Data
US 2019/0233877 A1  Aug. 1, 2019

Related U.S. Application Data

(60) Provisional application No. 62/411,998, filed on Oct. 24, 2016.

(51) Int. Cl.
*C12Q 1/6806* (2018.01)
*C40B 70/00* (2006.01)
(Continued)

(52) U.S. Cl.
CPC ........... *C12Q 1/6806* (2013.01); *C12N 15/10* (2013.01); *C12N 15/66* (2013.01); *C40B 70/00* (2013.01); *C40B 20/04* (2013.01)

(58) Field of Classification Search
CPC ...... C12Q 1/6806; C12N 15/10; C12N 15/66; C40B 70/00; C40B 20/04
See application file for complete search history.

(56) References Cited

U.S. PATENT DOCUMENTS

| | | | |
|---|---|---|---|
| 5,106,727 A | 4/1992 | Hartley et al. | |
| 5,508,169 A | 4/1996 | Deugau et al. | |

(Continued)

FOREIGN PATENT DOCUMENTS

| | | |
|---|---|---|
| CN | 102737167 A | 10/2012 |
| CN | 103154273 A | 6/2013 |

(Continued)

OTHER PUBLICATIONS

Genbank Accession No. AQ294731 HS_3037_A1_B06_MR CIT Approved Human Genomic Sperm Library D *Homo sapiens* genomic clone Plate=3037 col. 11 Row=C, genomic survey sequence; available Dec. 18, 2010; retrieved Mar. 8, 2022 from https://www.ncbi.nlm.nih.gov/nuccore/AQ294731 (Year: 2010).*

(Continued)

*Primary Examiner* — Jeremy C Flinders
(74) *Attorney, Agent, or Firm* — Michael Best & Friedrich LLP

(57) ABSTRACT

Methods related to concealment of genetic information present within nucleic acid sequences, wherein individual nucleic acid molecules are barcoded. In some embodiments barcoding occurs before, after, or during enrichment. Barcoded nucleic acids are then combined with control barcoded nucleic acids. Different methods are provided for barcoding and pooling to conceal different types of genetic information present within nucleic acids.

15 Claims, 6 Drawing Sheets

Specification includes a Sequence Listing.

(51) Int. Cl.
  *C40B 20/04* (2006.01)
  *C12N 15/10* (2006.01)
  *C12N 15/66* (2006.01)

(56) References Cited

U.S. PATENT DOCUMENTS

| | | | |
|---|---|---|---|
| 5,573,905 A | 11/1996 | Lerner et al. | |
| 5,604,097 A | 2/1997 | Brenner | |
| 5,635,400 A | 6/1997 | Brenner | |
| 5,654,413 A | 8/1997 | Brenner | |
| 5,695,934 A | 12/1997 | Brenner | |
| 5,763,175 A | 6/1998 | Brenner | |
| 5,963,722 A | 10/1999 | Carter | |
| 6,013,456 A | 1/2000 | Akhavan-Tafti | |
| 6,138,077 A | 10/2000 | Brenner | |
| 6,150,516 A | 11/2000 | Brenner et al. | |
| 6,312,911 B1 | 11/2001 | Bancroft et al. | |
| 6,352,828 B1 | 3/2002 | Brenner | |
| 6,417,010 B1 | 7/2002 | Cargill et al. | |
| 6,458,530 B1 | 10/2002 | Morris et al. | |
| 6,537,747 B1* | 3/2003 | Mills, Jr. et al. | 435/6 |
| 6,607,878 B2 | 8/2003 | Sorge | |
| 6,620,584 B1 | 9/2003 | Chee et al. | |
| 6,869,764 B2 | 3/2005 | Williams et al. | |
| 6,958,217 B2 | 10/2005 | Pedersen | |
| 7,056,676 B2 | 6/2006 | Korlach et al. | |
| 7,157,564 B1 | 1/2007 | Mittmann et al. | |
| 7,170,050 B2 | 1/2007 | Turner et al. | |
| RE39,571 E | 4/2007 | Cargill | |
| 7,217,522 B2 | 5/2007 | Brenner | |
| RE39,793 E | 8/2007 | Brenner | |
| 7,292,742 B2 | 11/2007 | Levene et al. | |
| 7,302,146 B2 | 11/2007 | Turner et al. | |
| 7,313,308 B2 | 12/2007 | Turner et al. | |
| 7,361,466 B2 | 4/2008 | Korlach et al. | |
| 7,371,519 B2 | 5/2008 | Wolber et al. | |
| 7,381,529 B2 | 6/2008 | Yamakawa et al. | |
| 7,407,757 B2 | 8/2008 | Brenner | |
| 7,416,844 B2 | 8/2008 | Korlach et al. | |
| 7,485,424 B2 | 2/2009 | Korlach et al. | |
| 7,537,897 B2 | 5/2009 | Brenner et al. | |
| 7,563,574 B2 | 7/2009 | Korlach et al. | |
| 7,659,070 B2 | 2/2010 | Williams et al. | |
| 7,698,250 B2 | 4/2010 | Dwork et al. | |
| 7,754,451 B2 | 7/2010 | Faham et al. | |
| 7,803,550 B2 | 9/2010 | Makarov | |
| 7,816,079 B2 | 10/2010 | Fischer | |
| 7,892,731 B2 | 2/2011 | Oliver et al. | |
| 7,901,891 B2 | 3/2011 | Drmanac | |
| 7,906,285 B2 | 3/2011 | Drmanac | |
| 7,910,302 B2 | 3/2011 | Drmanac et al. | |
| 7,939,256 B2 | 5/2011 | Williams | |
| 7,943,305 B2 | 5/2011 | Korlach et al. | |
| 7,943,307 B2 | 5/2011 | Korlach et al. | |
| 7,972,992 B2 | 7/2011 | Morgan et al. | |
| 8,039,214 B2 | 10/2011 | Dahl et al. | |
| 8,053,744 B2 | 11/2011 | Bortolin | |
| 8,071,312 B2 | 12/2011 | Makarov et al. | |
| 8,071,755 B2 | 12/2011 | Efcavitch et al. | |
| 8,073,666 B2 | 12/2011 | Fowler et al. | |
| RE43,097 E | 1/2012 | Albrecht et al. | |
| 8,093,063 B2 | 1/2012 | Albitar | |
| 8,133,672 B2 | 3/2012 | Bjornson et al. | |
| 8,148,516 B2 | 4/2012 | Williams et al. | |
| 8,309,330 B2 | 11/2012 | Travers et al. | |
| 8,340,914 B2 | 12/2012 | Gatewood et al. | |
| 8,399,199 B2 | 3/2013 | Makarov et al. | |
| 8,415,102 B2 | 4/2013 | Geiss et al. | |
| 8,445,205 B2 | 5/2013 | Brenner | |
| 8,518,640 B2 | 8/2013 | Drmanac et al. | |
| 8,530,154 B2 | 9/2013 | Williams | |
| 8,589,437 B1 | 11/2013 | Khomenko et al. | |
| 8,609,335 B2 | 12/2013 | Drmanac et al. | |
| 8,658,364 B2 | 2/2014 | Pham et al. | |
| 8,658,365 B2 | 2/2014 | Bjornson et al. | |
| 8,697,363 B2 | 4/2014 | Mir et al. | |
| 8,697,432 B2 | 4/2014 | Glover, III | |
| 8,709,725 B2 | 4/2014 | Turner et al. | |
| 8,728,737 B2 | 5/2014 | Makarov et al. | |
| 8,751,166 B2 | 6/2014 | Friedlander et al. | |
| 8,765,375 B2 | 7/2014 | Drmanac | |
| 8,765,379 B2 | 7/2014 | Drmanac | |
| 8,765,382 B2 | 7/2014 | Drmanac | |
| 8,771,950 B2 | 7/2014 | Church et al. | |
| 8,771,958 B2 | 7/2014 | Drmanac | |
| 8,812,243 B2 | 8/2014 | Cardonha et al. | |
| 8,855,935 B2 | 10/2014 | Myres et al. | |
| 8,906,614 B2 | 12/2014 | Wegener et al. | |
| 8,906,831 B2 | 12/2014 | Eid et al. | |
| 8,921,532 B2 | 12/2014 | Korlach | |
| 8,927,211 B2 | 1/2015 | Turner et al. | |
| 8,936,926 B2 | 1/2015 | Hanzel et al. | |
| 8,986,928 B2 | 3/2015 | Turner et al. | |
| 9,005,935 B2 | 4/2015 | Belyaev | |
| 9,023,769 B2 | 5/2015 | Drmanac et al. | |
| 9,045,798 B1 | 6/2015 | Williams et al. | |
| 9,074,204 B2 | 7/2015 | Anderson et al. | |
| 9,096,952 B2 | 8/2015 | Osborne et al. | |
| 9,116,118 B2 | 8/2015 | Turner et al. | |
| 9,163,053 B2 | 10/2015 | Siddiqi et al. | |
| 9,194,001 B2 | 11/2015 | Brenner | |
| 9,206,417 B2 | 12/2015 | Zahn et al. | |
| 9,222,122 B2 | 12/2015 | Swartz et al. | |
| 9,243,242 B2 | 1/2016 | Wang | |
| 9,315,806 B2 | 4/2016 | Lu et al. | |
| 9,315,857 B2 | 4/2016 | Fu et al. | |
| 9,328,382 B2 | 5/2016 | Drmanac et al. | |
| 9,336,177 B2 | 5/2016 | Hawthorne et al. | |
| 9,359,601 B2 | 6/2016 | Wagner | |
| 9,388,465 B2 | 7/2016 | Hindson et al. | |
| 9,410,150 B2 | 8/2016 | Brenner et al. | |
| 9,410,193 B2 | 8/2016 | Makarov et al. | |
| 9,410,200 B2 | 8/2016 | Balasubramanian et al. | |
| 9,464,107 B2 | 10/2016 | Wegener et al. | |
| 9,506,119 B2 | 11/2016 | Faham et al. | |
| 9,506,167 B2 | 11/2016 | Shetty et al. | |
| 9,512,478 B2 | 12/2016 | Bignell et al. | |
| 9,520,999 B2 | 12/2016 | Kievan et al. | |
| 9,523,129 B2 | 12/2016 | Faham et al. | |
| 9,528,107 B2 | 12/2016 | Pham et al. | |
| 9,542,527 B2 | 1/2017 | Travers et al. | |
| 9,567,639 B2 | 2/2017 | Oliphant et al. | |
| 9,574,189 B2 | 2/2017 | Franch et al. | |
| 9,582,640 B2 | 2/2017 | Travers et al. | |
| 9,598,727 B2 | 3/2017 | Makarov et al. | |
| 9,600,626 B2 | 3/2017 | Travers et al. | |
| 9,605,309 B2 | 3/2017 | Davis et al. | |
| 9,605,310 B2 | 3/2017 | Balasubramanian et al. | |
| 9,637,785 B2 | 5/2017 | Drmanac | |
| 9,677,119 B2 | 6/2017 | May et al. | |
| 9,695,468 B2 | 7/2017 | Hindson et al. | |
| 9,709,503 B2 | 7/2017 | Turner et al. | |
| 9,719,136 B2 | 8/2017 | Betts et al. | |
| 9,752,176 B2 | 9/2017 | Kung et al. | |
| 9,752,178 B2 | 9/2017 | Wu et al. | |
| 9,771,575 B2 | 9/2017 | Belyaev et al. | |
| 9,785,792 B2 | 10/2017 | Barrett et al. | |
| 9,809,847 B2 | 11/2017 | Kazakov et al. | |
| 9,824,068 B2 | 11/2017 | Wong | |
| 9,834,765 B2 | 12/2017 | Bergmann et al. | |
| 9,834,766 B2 | 12/2017 | Volkmuth et al. | |
| 9,834,814 B2 | 12/2017 | Peter et al. | |
| 9,840,732 B2 | 12/2017 | Anderson et al. | |
| 9,845,501 B2 | 12/2017 | Williams | |
| 9,850,482 B2 | 12/2017 | Kwon et al. | |
| 9,850,536 B2 | 12/2017 | Oliphant et al. | |
| 9,909,179 B2 | 3/2018 | Hamilton et al. | |
| 9,910,956 B2 | 3/2018 | Travers et al. | |
| 9,919,512 B2 | 3/2018 | Jung et al. | |
| 9,920,366 B2 | 3/2018 | Eltoukhy et al. | |
| 9,929,985 B1 | 3/2018 | Menkedick et al. | |
| 9,935,765 B2 | 4/2018 | Weaver et al. | |
| 9,942,206 B1 | 4/2018 | Miller et al. | |
| 9,944,980 B2 | 4/2018 | Rank et al. | |

(56) References Cited

U.S. PATENT DOCUMENTS

| | | |
|---|---|---|
| 9,957,564 B2 | 5/2018 | Li et al. |
| 9,996,778 B2 | 6/2018 | Church |
| 10,002,316 B2 | 6/2018 | Fodor et al. |
| 10,013,575 B2 | 7/2018 | Hubaux et al. |
| 10,017,759 B2 | 7/2018 | Kaper et al. |
| 10,025,791 B2 | 7/2018 | Lee |
| 10,036,007 B2 | 7/2018 | Bang et al. |
| 10,036,012 B2 | 7/2018 | Amorese et al. |
| 10,036,013 B2 | 7/2018 | Kim |
| 10,043,590 B2 | 8/2018 | Karvela et al. |
| 10,053,723 B2 | 8/2018 | Hindson et al. |
| 10,058,839 B2 | 8/2018 | Fan et al. |
| 10,077,473 B2 | 9/2018 | Asbury et al. |
| 10,081,836 B2 | 9/2018 | Clark et al. |
| 10,100,358 B2 | 10/2018 | Liu et al. |
| 10,102,927 B2 | 10/2018 | Downs et al. |
| 10,106,789 B2 | 10/2018 | Johnson et al. |
| 10,116,632 B2 | 10/2018 | Mishra et al. |
| 10,119,134 B2 | 11/2018 | Vigneault et al. |
| 10,119,975 B2 | 11/2018 | Shetty et al. |
| 10,125,391 B2 | 11/2018 | Turner et al. |
| 10,125,392 B2 | 11/2018 | Drmanac |
| 10,131,901 B2 | 11/2018 | Abrams et al. |
| 10,150,964 B2 | 12/2018 | Hindson et al. |
| 10,155,942 B2 | 12/2018 | Kurihara et al. |
| 10,161,002 B2 | 12/2018 | Korlach et al. |
| 10,162,678 B1 | 12/2018 | Stafford et al. |
| 10,169,538 B2 | 1/2019 | Ramachandran |
| 10,181,010 B2 | 1/2019 | Patel et al. |
| 10,190,115 B2 | 1/2019 | Saxonov |
| 10,190,155 B2 | 1/2019 | Amorese et al. |
| 10,190,163 B2 | 1/2019 | Conant et al. |
| 10,190,164 B2 | 1/2019 | Li et al. |
| 10,196,686 B2 | 2/2019 | Makarov et al. |
| 10,202,646 B2 | 2/2019 | Fodor et al. |
| 10,208,337 B2 | 2/2019 | Makarov et al. |
| 10,208,339 B2 | 2/2019 | Mir et al. |
| 10,214,770 B2 | 2/2019 | Robins et al. |
| 10,221,436 B2 | 3/2019 | Hardenbol et al. |
| 10,221,442 B2 | 3/2019 | Hindson et al. |
| 10,223,499 B2 | 3/2019 | Weaver et al. |
| 10,227,624 B2 | 3/2019 | Chen et al. |
| 10,233,490 B2 | 3/2019 | Stapleton et al. |
| 10,240,196 B2 | 3/2019 | Arezi et al. |
| 10,245,587 B2 | 4/2019 | Masquelier et al. |
| 10,246,702 B1 | 4/2019 | Richard et al. |
| 10,246,703 B2 | 4/2019 | Church et al. |
| 10,246,705 B2 | 4/2019 | Steemers et al. |
| 10,252,375 B2 | 4/2019 | Mori |
| 10,253,364 B2 | 4/2019 | Hindson et al. |
| 10,255,990 B2 | 4/2019 | Apte et al. |
| 10,266,874 B2 | 4/2019 | Weissleder et al. |
| 10,266,881 B2 | 4/2019 | Leamon et al. |
| 10,266,904 B2 | 4/2019 | Edwards |
| 10,272,432 B2 | 4/2019 | Ness et al. |
| 10,273,537 B2 | 4/2019 | Korlach et al. |
| 10,287,574 B2 | 5/2019 | Goryshin et al. |
| 10,287,623 B2 | 5/2019 | Jarosz et al. |
| 10,287,624 B2 | 5/2019 | Edelman |
| 10,289,801 B2 | 5/2019 | Church |
| 10,294,511 B2 | 5/2019 | Sanches-Kuiper et al. |
| 10,294,523 B2 | 5/2019 | Flusberg et al. |
| 10,296,709 B2 | 5/2019 | Laine et al. |
| 10,296,710 B2 | 5/2019 | Barber et al. |
| 10,296,842 B2 | 5/2019 | Lu et al. |
| 10,296,927 B2 | 5/2019 | Soria et al. |
| 10,301,677 B2 | 5/2019 | Shum et al. |
| 10,308,979 B2 | 6/2019 | Peter et al. |
| 10,316,345 B2 | 6/2019 | Tan et al. |
| 10,324,092 B2 | 6/2019 | Ciceri et al. |
| 10,325,067 B1 | 6/2019 | Suffin |
| 10,337,063 B1 | 7/2019 | Brenner et al. |
| 10,343,166 B2 | 7/2019 | Bharadwaj et al. |
| 10,344,318 B2 | 7/2019 | May et al. |
| 10,344,329 B2 | 7/2019 | Hindson et al. |
| 10,344,336 B2 | 7/2019 | Bramlett et al. |
| 10,347,365 B2 | 7/2019 | Wong et al. |
| 10,354,748 B1 | 7/2019 | Konerding et al. |
| 10,358,642 B2 | 7/2019 | Bang et al. |
| 10,364,464 B2 | 7/2019 | Nicol et al. |
| 10,366,777 B2 | 7/2019 | Kyriazopoulou-Panagiotopoulou et al. |
| 10,370,701 B2 | 8/2019 | Wilson |
| 2004/0142325 A1 | 7/2004 | Mintz et al. |
| 2006/0073487 A1 | 4/2006 | Oliver et al. |
| 2007/0020640 A1 | 1/2007 | McCloskey et al. |
| 2007/0042401 A1 | 2/2007 | Morgan et al. |
| 2007/0083334 A1* | 4/2007 | MIntz et al. .................... 702/19 |
| 2008/0268498 A1* | 10/2008 | Schoenfeld et al. ......... 435/68.1 |
| 2009/0275486 A1 | 11/2009 | Kurn et al. |
| 2010/0022403 A1 | 1/2010 | Kurn et al. |
| 2010/0069263 A1 | 3/2010 | Shendure et al. |
| 2012/0196279 A1 | 8/2012 | Underwood et al. |
| 2012/0220494 A1 | 8/2012 | Samuels et al. |
| 2013/0029855 A1 | 1/2013 | Seul |
| 2013/0273551 A1 | 10/2013 | Gilman |
| 2014/0206554 A1 | 7/2014 | Hindson et al. |
| 2014/0235506 A1 | 8/2014 | Hindson et al. |
| 2014/0242582 A1 | 8/2014 | Oliphant et al. |
| 2014/0255929 A1 | 9/2014 | Zheng |
| 2014/0256566 A1 | 9/2014 | Bergmann et al. |
| 2014/0322716 A1 | 10/2014 | Robins |
| 2015/0087556 A1 | 3/2015 | Ambros et al. |
| 2015/0133317 A1* | 5/2015 | Robinson et al. . C12N 15/1065 |
| 2015/0211050 A1 | 7/2015 | Iafrate et al. |
| 2015/0211061 A1 | 7/2015 | Iafrate et al. |
| 2015/0232929 A1 | 8/2015 | Stephens et al. |
| 2015/0329891 A1 | 11/2015 | Tan et al. |
| 2015/0337364 A1 | 11/2015 | Stahl et al. |
| 2016/0017320 A1 | 1/2016 | Wang et al. |
| 2016/0032396 A1 | 2/2016 | Diehn et al. |
| 2016/0053253 A1 | 2/2016 | Salathia et al. |
| 2016/0060621 A1 | 3/2016 | Agresti et al. |
| 2016/0108474 A1 | 4/2016 | Oliphant et al. |
| 2016/0115532 A1 | 4/2016 | Faham |
| 2016/0228841 A2 | 8/2016 | Fan et al. |
| 2016/0304860 A1 | 10/2016 | Hindson et al. |
| 2016/0304956 A1 | 10/2016 | Robins |
| 2017/0037469 A1 | 2/2017 | Robins et al. |
| 2017/0044525 A1 | 2/2017 | Kaper et al. |
| 2017/0058332 A1 | 3/2017 | Kermani et al. |
| 2017/0121716 A1 | 5/2017 | Rodi |
| 2017/0145476 A1 | 5/2017 | Ryvkin et al. |
| 2017/0166956 A1* | 6/2017 | Driscoll et al. ...... C12Q 1/6806 |
| 2017/0191126 A1 | 7/2017 | Ronaghi et al. |
| 2017/0198345 A1 | 7/2017 | Frenz et al. |
| 2017/0260584 A1 | 9/2017 | Zheng et al. |
| 2017/0292149 A1 | 10/2017 | Sherwood et al. |
| 2017/0321271 A1 | 11/2017 | Hubbell |
| 2018/0010120 A1 | 1/2018 | Mellor et al. |
| 2018/0105808 A1 | 4/2018 | Mikkelsen et al. |
| 2018/0127816 A1 | 5/2018 | Teo et al. |
| 2018/0291427 A1 | 10/2018 | Edelman |
| 2018/0371525 A1 | 12/2018 | Lebofsky et al. |
| 2019/0071711 A1 | 3/2019 | Bibillo et al. |
| 2019/0136307 A1 | 5/2019 | Predki et al. |
| 2019/0136309 A1 | 5/2019 | Church et al. |
| 2019/0194739 A1 | 6/2019 | Efcavitch et al. |
| 2019/0233877 A1 | 8/2019 | Sawaya |

FOREIGN PATENT DOCUMENTS

| | | |
|---|---|---|
| CN | 104812947 A | 7/2015 |
| WO | WO 2000/068431 A2 | 11/2000 |
| WO | 2009001135 A2 | 12/2008 |
| WO | 2015/117145 A1 | 8/2015 |
| WO | 2015117145 A1 | 8/2015 |
| WO | WO 2016/133911 A1 | 8/2016 |
| WO | 2017100496 A1 | 6/2017 |
| WO | WO 2018/081113 A1 | 5/2018 |

(56) References Cited

OTHER PUBLICATIONS

Genbank Accession No. AQ218321 HS_3245_A2_E11_T7 CIT Approved Human Genomic Sperm Library D *Homo sapiens* genomic clone Plate=3245 col. 22 Row=1, genomic survey sequence; available Dec. 19, 2010; retrieved Mar. 8, 2022 from https://www.ncbi.nlm.nih.gov/nuccore/AQ218321 (Year: 2010).*

Genbank Accession No. AQ212264 HS_2240_A2_A02_MR CIT Approved Human Genomic Sperm Library D *Homo sapiens* genomic clone Plate=2240 col. 4 Row=A, genomic survey sequence; available Dec. 18, 2010; retrieved Mar. 8, 2022 from https://www.ncbi.nlm.nih.gov/nuccore/AQ212264 (Year: 2010).*

Genbank Accession No. AQ764974 HS_3199_B2_A09_MR CIT Approved Human Genomic Sperm Library D *Homo sapiens* genomic clone Plate=3199 col. 18 Row=B, genomic survey sequence; available Dec. 18, 2010; retrieved Mar. 8, 2022 from https://www.ncbi.nlm.nih.gov/nuccore/AQ764974 (Year: 2010).*

European Patent Office Extended Search Report for Application No. 17865703.7 dated Apr. 2, 2020 (7 pages).

Quail et al., "SASI-Seq: sample assurance Spike-Ins, and highly differentiating 384 barcoding for Illumina sequencing," BMC Genomics, 2014, 15(1):110, 13 pages.

Canadian Patent Office Action for Application No. 3,041,645 dated Jun. 4, 2020 (5 pages).

International Search Report and Written Opinion for Application No. PCT/US2017/058076 dated Mar. 5, 2018 (9 pages).

Ahmad et al., "A Robotics Platform for Automated Batch Fabrication of High Density, Microfluidics-Based DNA Microarrays, with Applications to Single Cell, Multiplex Assays of Secreted Proteins." Review of Scientific Instruments, vol. 82, No. 9, 2011, 094301, 8 pages.

Anwar et al., "DNA Cryptography Based on Symmetric Key Exchange." International Journal of Engineering and Technology, vol. 7, No. 3, 2015, pp. 938-950.

Atas et al., "DNA Sequencing and Bar-Coding Using Solid-State Nanopores." Electrophoresis, vol. 33, No. 23, 2012, pp. 3437-3447.

Atkins et al., "Ribosomal Frameshifting and Transcriptional Slippage: From Genetic Steganography and Cryptography to Adventitious Use." Nucleic Acids Research, 2016, 44(15):7007-7078.

Balog et al., "Decoding DNA Labels by Melting Curve Analysis Using Real-Time PCR." BioTechniques, vol. 63, No. 6, 2017, 261-266.

Berry et al., "Barcoded Primers Used in Multiplex Amplicon Pyrosequencing Bias Amplification." Applied and Environmental Microbiology, vol. 77, No. 21, 2011, pp. 7846-7849.

Borgström, Erik, et al. "Phasing of Single DNA Molecules by Massively Parallel Barcoding." Nature Communications, vol. 6, No. 1, 2015, 6 pages.

Brukner et al., "Generation of Amplifiable Genome-Specific Oligonucleotide Probes and Libraries." BioTechniques, vol. 33, No. 4, 2002, pp. 874-882.

Buschmann et al., "Enhancing the Detection of Barcoded Reads in High Throughput DNA Sequencing Data by Controlling the False Discovery Rate." BMC Bioinformatics, vol. 15, No. 1, 2014, Article 264, 16 pages.

Carter, "Site-Directed Mutagenesis." Biochemical Journal, vol. 237, No. 1, 1986, pp. 1-7.

Cassa et al., "A Novel, Privacy-Preserving Cryptographic Approach for Sharing Sequencing Data." Journal of the American Medical Informatics Association, vol. 20, No. 1, 2012, pp. 69-76.

Çetin et al., "Private Queries on Encrypted Genomic Data." BMC Medical Genomics, vol. 10, No. S2, 2017, Article 45, 14 pages.

Chen et al., "Efficient in Situ Barcode Sequencing Using Padlock Probe-Based BaristaSeq." Nucleic Acids Research, vol. 46, No. 4, 2017, e22.

Clayton, "On Inferring Presence of an Individual in a Mixture: a Bayesian Approach." Biostatistics, vol. 11, No. 4, 2010, pp. 661-673.

Cook et al., "Systematic Validation and Atomic Force Microscopy of Non-Covalent Short Oligonucleotide Barcode Microarrays." PLoS One, vol. 3, No. 2, 2008, e1546, 14 pages.

Cui et al., "An Encryption Scheme Using DNA Technology," 2008 3rd International Conference on Bio-Inspired Computing: Theories and Applications, BICTA 2008, pp. 37-42.

Danaher et al., "Facile Semi-Automated Forensic Body Fluid Identification by Multiplex Solution Hybridization of NanoString® Barcode Probes to Specific MRNA Targets." Forensic Science International: Genetics, vol. 14, 2015, pp. 18-30.

Demaree et al., "An Ultrahigh-Throughput Microfluidic Platform for Single-Cell Genome Sequencing: Protocol." JoVE (Journal of Visualized Experiments), 2018, 135:e57598, 13 pages.

Erlich et al., "DNA Sudoku—Harnessing High-Throughput Sequencing for Multiplexed Specimen Analysis." Genome Research, vol. 19, No. 7, 2009, pp. 1243-1253.

Erlich et al., "Routes for Breaching and Protecting Genetic Privacy." Nature Reviews Genetics, vol. 15, No. 6, 2014, pp. 409-421.

Faircloth et al., "Not All Sequence Tags Are Created Equal: Designing and Validating Sequence Identification Tags Robust to Indels." PloS One, 2012, 7(8):e42543, 11 pages.

Ficetola et al., "An In Silico Approach for the Evaluation of DNA Barcodes." BMC Genomics, vol. 11, No. 1, 2010, Article 434, 10 pages.

Frank, "Barcrawl and Bartab: Software Tools for the Design and Implementation of Barcoded Primers for Highly Multiplexed DNA Sequencing." BMC Bioinformatics, vol. 10, No. 1, 2009, Article 362, 13 pages.

Freitag et al., "Visualizing the Entire DNA from a Chromosome in a Single Frame." Biomicrofluidics, vol. 9, No. 4, 2015, Article 044114, 10 pages.

Fu et al., "Counting Individual DNA Molecules by the Stochastic Attachment of Diverse Labels." Proceedings of the National Academy of Sciences, vol. 108, No. 22, 2011, pp. 9026-9031.

Gansauge et al., "Single-Stranded DNA Library Preparation from Highly Degraded DNA using T4 DNA Ligase." Nucleic Acids Research, 2017, 45(10):e79, 10 pages.

Gharizadeh et al., "Large-Scale Pyrosequencing of Synthetic DNA: A Comparison with Results from Sanger Dideoxy Sequencing." Electrophoresis, vol. 27, No. 15, 2006, pp. 3042-3047.

Goldstein, Leonard D., et al. "Massively Parallel Nanowell-Based Single-Cell Gene Expression Profiling." BMC Genomics, vol. 18, No. 1, 2017, Article 519, 10 pages.

Gregory et al., "Targeted Single Molecule Mutation Detection with Massively Parallel Sequencing." Nucleic Acids Research, vol. 44, No. 3, 2015, Article e22, 11 pages.

Gueidan et al., "PacBio Amplicon Sequencing for Metabarcoding of Mixed DNA Samples from Lichen Herbarium Specimens." MycoKeys, vol. 53, 2019, pp. 73-91.

Gunderson et al., "Decoding Randomly Ordered DNA Arrays," Genome Research, 2004, 14:870-877.

Hall et al., "Design, Synthesis, and Amplification of DNA Pools for In Vitro Selection." Current Protocols in Molecular Biology, 2009, Unit 24.2, 27 pages.

Halvorsen et al., "Binary DNA Nanostructures for Data Encryption." PLoS One, vol. 7, No. 9, 2012, Article e44212, 4 pages.

Hawkins et al., "Indel-Correcting DNA Barcodes for High-Throughput Sequencing." Proceedings of the National Academy of Sciences, vol. 115, No. 27, 2018, E6217-E6226.

Heckel et al., "A Characterization of the DNA Data Storage Channel." Scientific Reports, vol. 9, No. 1, 2019, Article 9663, 12 pages.

Kantarcioglu et al., "A Cryptographic Approach to Securely Share and Query Genomic Sequences." IEEE Transactions on Information Technology in Biomedicine, vol. 12, No. 5, 2008, pp. 606-617.

Kivioja et al., "Counting Absolute Numbers of Molecules Using Unique Molecular Identifiers." Nature Methods, vol. 9, No. 1, 2011, 18 pages.

Kracht et al., "Insertion and Deletion Correcting DNA Barcodes Based on Watermarks." BMC Bioinformatics, vol. 16, No. 1, 2015, Article 50, 14 pages.

Krehenwinkel et al., "Nanopore Sequencing of Long Ribosomal DNA Amplicons Enables Portable and Simple Biodiversity Assess-

(56) References Cited

OTHER PUBLICATIONS ments with High Phylogenetic Resolution across Broad Taxonomic Scale." GigaScience, vol. 8, No. 5, 2019, 16 pages.
Kukita et al., "High-Fidelity Target Sequencing of Individual Molecules Identified Using Barcode Sequences:De Novodetection and Absolute Quantitation of Mutations in Plasma Cell-Free DNA from Cancer Patients." DNA Research, vol. 22, No. 4, 2015, pp. 269-277.
Lan et al., "Droplet Barcoding for Massively Parallel Single-Molecule Deep Sequencing." Nature Communications, vol. 7, No. 1, 2016, Article 11784, 10 pages.
Lan et al., "Single-Cell Genome Sequencing at Ultra-High-Throughput with Microfluidic Droplet Barcoding." Nature News, Nature Publishing Group, 2017, 35(7):640-646.
Lanner et al., "Illumina Midi-Barcodes: Quality Proof and Applications." Mitochondrial DNA Part A, vol. 30, No. 3, 2019, pp. 490-499.
Lee et al., "Mutation Analysis of Synthetic DNA Barcodes in a Fission Yeast Gene Deletion Library by Sanger Sequencing." Genomics & Informatics, vol. 16, No. 2, 2018, pp. 22-29.
Lee et al., "Terminator-Free Template-Independent Enzymatic DNA Synthesis for Digital Information Storage." Nature Communications, vol. 10, No. 1, 2019, Article 2383, 12 pages.
Lyons et al., "Large-Scale DNA Barcode Library Generation for Biomolecule Identification in High-Throughput Screens." Nature News, Nature Publishing Group, 2017, 7:13899, 7 pages.
Matochko et al., "Deep Sequencing Analysis of Phage Libraries Using Illumina Platform." Methods, vol. 58, No. 1, 2012, pp. 47-55.
Mezger et al., "Highly Specific DNA Detection Employing Ligation on Suspension Bead Array Readout." New Biotechnology, vol. 32, No. 5, 2015, pp. 504-510.
Mondal et al., "Review on DNA Cryptography". arXiv:1904.05528, 2019, 31 pages.
Motea et al., "Terminal Deoxynucleotidyl Transferase: The Story of a Misguided DNA Polymerase." Biochimica Et Biophysica Acta (BBA)—Proteins and Proteomics, vol. 1804, No. 5, 2010, pp. 1151-1166.
Nguyen et al., "Real-Time Demultiplexing Nanopore Barcoded Sequencing Data with NpBarcode." Bioinformatics, vol. 33, No. 24, 2017, pp. 3988-3990.
Parameswaran et al., "A Pyrosequencing-Tailored Nucleotide Barcode Design Unveils Opportunities for Large-Scale Sample Multiplexing." Nucleic Acids Research, vol. 35, No. 19, 2007, Article e130, 9 pages.
Peikon et al., "In Vivo Generation of DNA Sequence Diversity for Cellular Barcoding." Nucleic Acids Research, Oxford University Press, 2014, 42(16):e127, 10 pages.
Ranu et al., "Targeting Individual Cells by Barcode in Pooled Sequence Libraries." Nucleic Acids Research, vol. 47, No. 1, 2018, Article e4, 7 pages.
Redin et al., "Droplet Barcode Sequencing for Targeted Linked-Read Haplotyping of Single DNA Molecules." Nucleic Acids Research, vol. 45, No. 13, 2017, Article e125, 8 pages.
Sawaya, "Cryptography for Genetic Material." BioRxiv, 2018, 25 pages.
Shearer et al., "Pre-Capture Multiplexing Improves Efficiency and Cost-Effectiveness of Targeted Genomic Enrichment." BMC Genomics, vol. 13, No. 1, 2012, Article 618, 8 pages.
Shearer et al., "Solution-Based Targeted Genomic Enrichment for Precious DNA Samples." BMC Biotechnology, vol. 12, No. 1, 2012, Article 20, 6 pages.
Shokralla et al., "Massively Parallel Multiplex DNA Sequencing for Specimen Identification Using an Illumina MiSeq Platform." Scientific Reports, vol. 5, No. 1, 2015, Article 9687, 7 pages.
Shokralla et al., "Next-Generation DNA Barcoding: Using next-Generation Sequencing to Enhance and Accelerate DNA Barcode Capture from Single Specimens." Molecular Ecology Resources, vol. 14, No. 5, 2014, pp. 892-901.
Smith et al., "Quantitative phenotyping via deep barcode sequencing," Genome Research, 2009, 19:1836-1842.

Smith et al., "Highly-Multiplexed Barcode Sequencing: an Efficient Method for Parallel Analysis of Pooled Samples." Nucleic Acids Research, vol. 38, No. 13, 2010, Article e142, 7 pages.
Srivathsan et al., "A MinION™-Based Pipeline for Fast and Cost-Effective DNA Barcoding." Molecular Ecology Resources, vol. 18, No. 5, 2018, pp. 1035-1049.
Stiller et al., "Direct Multiplex Sequencing (DMPS)—a Novel Method for Targeted High-Throughput Sequencing of Ancient and Highly Degraded DNA." Genome Research, vol. 19, No. 10, 2009, pp. 1843-1848.
Sukumaran et al., "PCR and Bio-Signature for Data Confidentiality and Integrity in Mobile Cloud Computing." Journal of King Saud University—Computer and Information Sciences, 2018, 10 pages.
Summerbell et al., "Microcoding: the Second Step in DNA Barcoding." Philosophical Transactions of the Royal Society B: Biological Sciences, vol. 360, No. 1462, 2005, pp. 1897-1903.
Tabler, "Representation of Unique Sequences in Libraries of Randomized Nucleic Acids." Nucleic Acids Research, vol. 24, No. 17, 1996, pp. 3437-3438.
Tambe et al., "Barcode Identification for Single Cell Genomics." BMC Bioinformatics, vol. 20, 2019, Article 32, 9 pages.
Tang et al., "Enzymatic Polymerization of High Molecular Weight DNA Amphiphiles That Self-Assemble into Star-Like Micelles." Advanced Materials, vol. 26, No. 19, 2014, pp. 3050-3054.
Tang, "Enzymatic Polymerization of High Molecular Weight DNA," Dissertation, 2016, 163 pages.
Tedersoo et al., "PacBio Metabarcoding of Fungi and Other Eukaryotes: Errors, Biases and Perspectives." New Phytologist, vol. 217, No. 3, 2017, pp. 1370-1385.
Thielecke et al., "Limitations and Challenges of Genetic Barcode Quantification." Scientific Reports, vol. 7, No. 1, 2017, Article 43249, 14 pages.
Trébeau et al., "DNABarcodeCompatibility: an R-Package for Optimizing DNA-Barcode Combinations in Multiplex Sequencing Experiments." Bioinformatics, vol. 35, No. 15, 2018, pp. 2690-2691 . . . .

Uzbas et al., "BART-Seq: Cost-Effective Massively Parallelized Targeted Sequencing for Genomics, Transcriptomics, and Single-Cell Analysis." Genome Biology, 2019, 20:155, 16 pages.
Wang et al., "Efficient and Unique Cobarcoding of Second-Generation Sequencing Reads from Long DNA Molecules Enabling Cost-Effective and Accurate Sequencing, Haplotyping, and De Novo Assembly." Genome Research, vol. 29, No. 5, 2019, pp. 798-808.
Warner et al., "Rapid Profiling of a Microbial Genome Using Mixtures of Barcoded Oligonucleotides." Nature Biotechnology, vol. 28, No. 8, 2010, pp. 856-862.
Wen et al., "Evaluation of the Reproducibility of Amplicon Sequencing with Illumina MiSeq Platform." Plos One, vol. 12, No. 4, 2017, Article e0176716, 20 pages.
Wick et al., "Deepbinner: Demultiplexing Barcoded Oxford Nanopore Reads with Deep Convolutional Neural Networks." PLoS Comput Biol, 2018, 14(11):e1006583, 11 pages.
Wong et al., "Multiplex Illumina Sequencing Using DNA Barcoding." Current Protocols in Molecular Biology, 2013, Unit 7.11, 11 pages.
Xu et al., "Design of 240,000 Orthogonal 25mer DNA Barcode Probes." Proceedings of the National Academy of Sciences, vol. 106, No. 7, 2009, pp. 2289-2294.
Zahariev et al., "Efficient algorithms for the discovery of DNA oligonucleotide barcodes from sequence databases," Molecular Ecology Resources, 2009, 9(Suppl. 1):58-64.
Zahra et al., "Forensic STR Profiling Based Smart Barcode, a Highly Efficient and Cost Effective Human Identification System." Saudi Journal of Biological Sciences, vol. 25, No. 8, 2018, pp. 1720-1723.
Zheng et al., "Anchored Multiplex PCR for Targeted next-Generation Sequencing." Nature Medicine, vol. 20, No. 12, 2014, pp. 1479-1486.
Zimmermann et al., "DNA-Encoded Chemical Libraries: Foundations and Applications in Lead Discovery." Drug Discovery Today, vol. 21, No. 11, 2016, pp. 1828-1834.

(56) References Cited

OTHER PUBLICATIONS

Zizka, et al., "Assessing the Influence of Sample Tagging and Library Preparation on DNA Metabarcoding." Molecular Ecology Resources, vol. 19, No. 4, 2019, pp. 893-899.

Canadian Intellectual Property Office Action for Application No. 3,041,645 dated Nov. 23, 2020 (3 pages).

Israeli Patent Office action for Application No. 266197 dated May 24, 2022 (4 pages).

China National Intellectual Property Administration Notification of First Office Action for Application No. 201780073821.X dated Apr. 11, 2022 (21 pages including English translation).

Intellectual Property India Patent Office Examination Report for Application No. 201917016342 dated Jan. 24, 2023 (7 pages including English translation).

\* cited by examiner

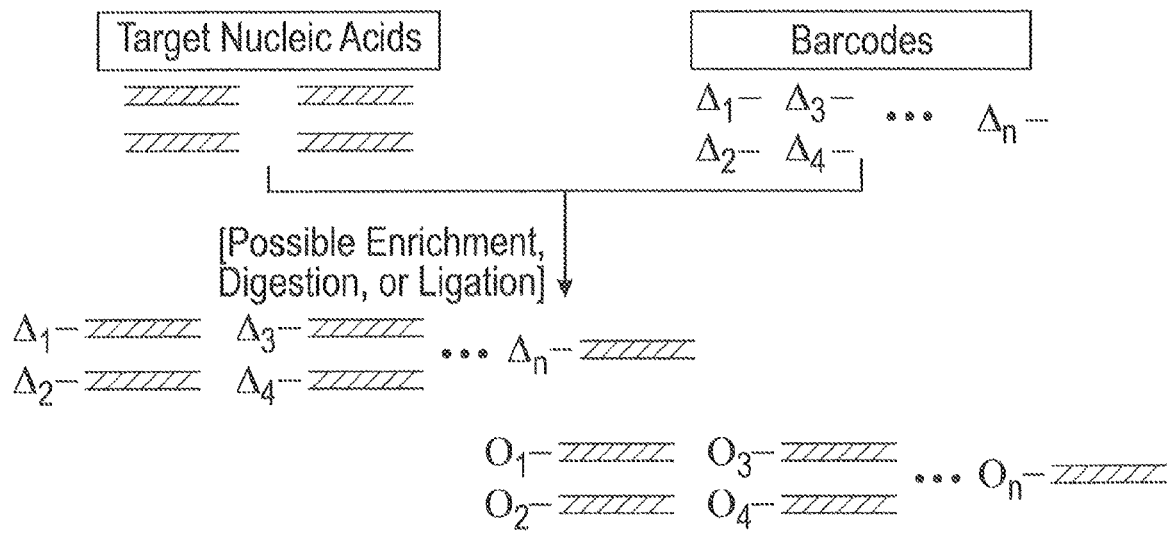
FIG. 1A
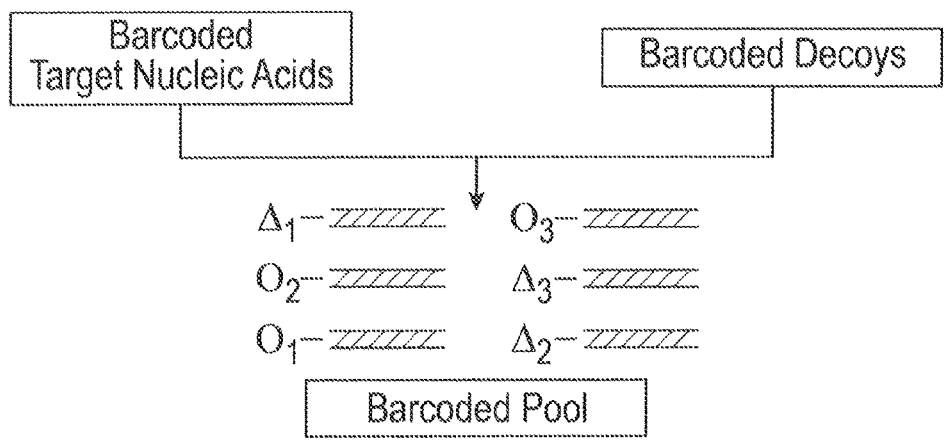
FIG. 1B
Table of Barcodes
| $\Delta_1$ | Target | $O_1$ | Decoy |
| $\Delta_2$ | Target | $O_2$ | Decoy |
| ⋮ | | ⋮ | |
| $\Delta_n$ | Target | $O_n$ | Decoy |
FIG. 1C

Set of Possible Barcodes

$$\left\{ \begin{array}{c|cccc} 1 & A\,A\,A & \cdots & A & b_1 \\ 2 & A\,A\,A & \cdots & T & b_2 \\ 3 & A\,A\,A & \cdots & C & \\ \vdots & & & & \\ 4^m & G\,G\,G & \cdots & G & b_b \end{array} \right\}$$

Possible Set Size $4^m$

Where "m" is Length of Barcodes

---

Set of Usable Barcodes

$$\left\{ \begin{array}{c|cccc} 1 & A\,T\,A & \cdots & A \\ 2 & A\,T\,A & \cdots & T \\ 3 & A\,T\,A & \cdots & C \\ \vdots & & & \\ n & G\,C\,G & \cdots & G \end{array} \right\}$$ Bad Barcodes Removed ($b_1 \cdots b_b$) with "b" Bad Barcodes Set of Usable Barcodes Size $n \cong 4^m - b$

---

"n" is Very Large as "m" Increases Because $4^m \gg b$

FIG. 3

CONCEALING INFORMATION PRESENT WITHIN NUCLEIC ACIDS

CROSS-REFERENCE TO RELATED APPLICATION(S)

This application is a U.S. national stage entry of International Patent Application No. PCT/US2017/058076, filed on Oct. 24, 2017, which claims priority to U.S. Provisional Patent Application No. 62/411,998, filed on Oct. 24, 2016, the entire contents of each of which are fully incorporated herein by reference.

INCORPORATION-BY-REFERENCE OF MATERIAL SUBMITTED ELECTRONICALLY

Incorporated herein by reference in its entirety is a computer-readable nucleotide/amino acid sequence listing submitted concurrently herewith and identified as follows: One 1,043 Byte ASCII (Text) file named "213817-9002-US02_ST25.txt," created on Apr. 22, 2019.

BACKGROUND

Nucleic acids can provide genetic information about an organism from which the nucleic acids originated (e.g. disease risk). This genetic information can be used to identify an individual, thus providing a challenge for obtaining genetic information while maintaining privacy of an individual. For example, genetic association study participants may be identifiable, and their disease risk estimated, using the data from the association study. This may also provide a challenge for the use of nucleic acids in clinical assessments, as patients may fear being identified when undergoing a genetic test. The concealment of nucleic acids may also be of interest to plant and/or animal breeders. These breeders may seek genetic information from nucleic acids of their breeds, but may also have an interest in concealing information about those breeds and/or breeding methods. Similarly, those developing microbes for industrial and/or medical purposes may benefit from concealing nucleic acids from potential adversaries. Also, the use of nucleic acids as data storage mediums may warrant concealment of the information being stored as nucleic acids.

To mitigate issues related to genomic privacy in humans, researchers have proposed various solutions, including: informed consent, encryption of genomic data, limits on the sharing of genomic data, and the ability for subjects to opt out of databases. All of these methods are only applied to nucleic acid sequence data, not to nucleic acids themselves.

Methods for maintaining privacy of nucleic acids prior to their analysis are severely lacking. Prior to analysis, individual samples can have their nucleic acids tagged with a barcode, identifying the entire sample with a single barcode. By pooling these samples, and only identifying them with the barcode (and not a name or other identifier), some limited concealment is provided. However, an adversary with access to the sequence data would be able to directly observe the number of samples that were pooled, and would know the genotypes of each sample. These genotypes could then be used to identify the origins of the samples, and make predictions about traits of the samples.

Additionally, nucleic acids can be used as a data storage medium. In such instances, the data requires a sequencer to retrieve and/or convert the medium of the data (e.g. to a digital format). Concealment of the data stored in nucleic acids would be useful if an adversary had access to the sequence data. In these or similar circumstances, obfuscating and concealing the type or form of data present in the nucleic acids may be useful.

There is therefore an unmet need for methods of concealing nucleic acids themselves, prior to analysis. By concealing nucleic acids, they could then be sent for analysis by a third party while minimizing the information provided from the nucleic acids of interest.

BRIEF SUMMARY OF THE INVENTION

The technology described herein relates to the preparation of nucleic acids. The methods described herein relate to concealment of nucleic acids prior to analyses (e.g. sequencing). In some embodiments, the identity of the source of the nucleic acids is concealed, anonymizing the nucleic acids. In some embodiments, the presence of nucleic acids is concealed. In some embodiments, the information contained within nucleic acids relating to traits of an organism are concealed. In some embodiments, the potential purpose for analyzing the nucleic acids is concealed. In some embodiments, information is concealed within nucleic acids that are being used as an information storage medium. In some embodiments, the methods described herein relate to enrichment of nucleic acids prior to analysis.

In one aspect, the technology described herein relates to a method of preparing nucleic acids prior to sequence analysis, such that the nucleic acids are concealed and/or obfuscated and/or anonymized. The method comprises:
(a) Generating a set of barcodes composed of nucleic acids in a secure facility, and delivering them to a consumer, such that the properties of the barcodes are hidden to everyone except the consumer;
(b) Affixing the barcodes to nucleic acids that are to be analyzed; and,
(c) Combining the barcoded nucleic acids with other barcoded nucleic acids to conceal their information prior to analysis.

Methods for Generating Materials Securely in Step (a)

In some embodiments, the barcodes and their relevant adapters, indexes, or other nucleic acids or chemicals that function to help conceal nucleic acids, are generated in a facility that is ensured to be free from any monitoring device and that does not have any form of communication outside of the secured facility. In some embodiments, the secure facility is surrounded by electromagnetic shielding, such as a faraday cage, to prevent unwanted electromagnetic communication. In some embodiments, equipment and machinery within the facility is surrounded by electromagnetic shielding. In some embodiments, the secure facility would lack communication cables outside of the facility, such as copper phone lines or fiber optic cables. In some embodiments, electronic devices in such a facility would lack any connection to anything outside of the facility, and would be "air-gapped" from the outside world. In some embodiments, individuals working in the facility would not be allowed recording devices of any kind, such as cameras. In some embodiments, the secure facility exists as a building, while in other embodiments the secure facility exists as a room or collection of rooms within a building.

In some embodiments, a set of barcode sequences would be generated randomly by a computer, ensuring that each barcode in the set is unique and that knowledge about any barcodes in the set would not enable prediction in any form about the other barcodes in the set. In some embodiments, knowledge about some barcodes in a set of barcodes can be used to make a limited amount of prediction about the sequences of other barcodes in the set. In such embodiments, the amount of prediction about a set of barcodes that is permissible for a given security environment can, in some embodiments, be measured by those skilled in the art. This set of barcodes would then be divided into a number of subsets. Each subset would be labeled with a unique identifier, and a table matching these identifiers to the barcodes would also be generated on a computer. The table of barcodes would be placed on a secure data transfer device, such as CD-ROM, DVD-ROM, or flash memory drive. In some embodiments, the barcode identifying table is also printed on a medium such as paper.

In some embodiments, the set of barcodes is examined prior to the generation of barcodes to ensure that the sequences of barcodes are unlikely to interfere with their use in any further steps in the invention. This comparison can be achieved by a computer program which can be generated by methods known to those skilled in the art. In some embodiments, the sequences of barcodes that are not ideal for use are generated prior to the generation of any barcode sequences, and are used to filter the set of barcode sequences prior to generation of the barcodes.

In some embodiments, the information about the barcodes would be transferred to the machines used to generate the barcodes along with their relevant adapters, indexes or other materials used in this technology. All information transfer between any machines and/or computers would take place using a wire that is shielded from electromagnetic radiation, preventing information from leaking from the wire. In other embodiments, the computer that generates the random set of barcodes is incorporated into the machine or machines that are used to generate the random barcodes. In such embodiments, shielding of the entire machine from electromagnetic radiation would prevent information about the barcodes from being detected.

The barcodes and their related materials would be generated and placed in their own container, such as a test-tube or in a well in a micro-well plate. These containers are labeled and/or identified so that the barcode identities can be looked up using the table of barcodes generated by the computer.

In some embodiments, the subsets of barcoded materials are placed in a container, along with its table of barcodes. This container is then sealed in such a way as to indicate whether it has been opened or otherwise tampered with, using, for example, seals that cannot be resealed after the box has been opened. In some embodiments, this container may also contain other nucleic acids that may be used to pool with nucleic acids in further steps of the technology. In some embodiments, the nucleic acids that are included may be barcoded, may be partially barcoded, or may not have barcodes added. In some embodiments, software and/or files used to direct the use of this technology are provided in this container.

In some embodiments, the barcodes are not entirely unique. In some embodiments, the subsets of barcodes contain some barcodes that are present in other subsets. In some of these embodiments, the generation of these sets of not-entirely-unique barcodes can again be directed by a computer. In other embodiments, the barcodes are generated entirely randomly in such a way that their sequences are known, in part or in full, and the information about the barcode sequences is recorded securely. In these embodiments, the information about the randomly generated barcodes would be securely placed on a secure data transfer device, such as CD-ROM, DVD-ROM, or flash memory drive. In these embodiments, the true randomness of the barcode generation would be checked to ensure that knowledge of some barcodes in the set would not provide information about other barcodes in the set, or would only provide minimal information about other barcodes to meet security standards required by the consumer. In these embodiments, a filtration process by which undesirable barcodes can be removed is applied to each group of barcodes to ensure that the barcodes will not interfere with further steps in the invention.

Methods for Barcoding in Step (b)

In some embodiments, barcodes are added to nucleic acids prior to or during enrichment using technology described by U.S. patent publication US 2015/0211050, and U.S. patent publication 2015/0211061, both of which are incorporated herein by reference.

In some embodiments, barcodes are added by ligation and enrichment does not subsequently occur. In some embodiments, barcoding by ligation may occur when barcodes are already present. In some embodiments, the barcode molecule contains an adapter that facilitates ligation of the barcode with other nucleic acids. In some embodiments, barcodes with adapters can be ligated using sticky-end ligation, e.g. TA-ligation.

In some embodiments, restriction enzymes are used to digest nucleic acids prior to their barcoding. In some embodiments, restriction enzyme digestion generates sticky-ends. In these embodiments, the adapters on the barcodes contain sticky ends that correspond to the sticky ends generated by the restriction enzymes, facilitating ligation of the barcodes.

In some embodiments, not all target and/or decoy nucleic acids are barcoded. In some embodiments, a random quantity of nucleic acids are barcoded. In some embodiments, the randomness intrinsic to molecular biology techniques is utilized for randomly barcoding some of the nucleic acids. In some embodiments, a computer is utilized to estimate the quantity of barcoding necessary to obtain requisite information from target nucleic acids and compare barcoding and pooling methods to estimate the privacy obtained by such methods. In some embodiments, a computer directs a random proportion of nucleic acids to be barcoded.

Methods for Combining Barcoded Nucleic Acids in Step (c)

In some embodiments, the barcoded nucleic acids to be concealed are pooled with similar barcoded nucleic acids (i.e., a control and/or decoy nucleic acid sequence). For example, control nucleic acids may be nucleic acids that originated from the same genes in the same species, but from different individuals. In some embodiments, the pooled nucleic acids are similar to nucleic acids that would be found in a relevant population and also similar to the nucleic acids to be concealed. For example, nucleic acids originating from the same gene and from the same ethnic group within a population. In some embodiments, the barcoded nucleic acids are pooled with other barcoded nucleic acids that contain a relatively high ratio of nucleic acids that may signify a potential trait. For example, the barcoded nucleic acids would be pooled with barcoded nucleic acids that have a high proportion of a disease carrying variant, higher than the proportion of disease carrying variants than would be found in an ethnically matched population.

In some embodiments, the parents and/or other individuals closely related to the source of the nucleic acids to be concealed are barcoded and pooled with the barcoded nucleic acids to be concealed. In some embodiments, a much higher amount of nucleic acids from the relatives are used than the amount of nucleic acids that are to be concealed. In some embodiments, the relative quantities of different nucleic acids are modified such that their proportions are dissimilar between different relatives and the nucleic acids to be concealed. In some embodiments, a group of nucleic acids that are to be concealed are barcoded and pooled with each other. In some embodiments, a group of nucleic acids that are not to be concealed, and are of no interest to the consumer, are pooled with the barcoded nucleic acids of interest. In such embodiments, the pool of nucleic acids that is pooled with the nucleic acids of interest is well controlled. In these instances, specific nucleic acids may be chosen to optimize concealment. In such embodiments, a large amount of uninteresting analyses are conducted in order to conceal the analyses of nucleic acids of interest.

In some embodiments, nucleic acids are being used to store data, for example the use of deoxyribonucleic acids as a data storage medium. In some embodiments, these data-storing nucleic acids are barcoded and pooled with other data-storing nucleic acids. In some embodiments, these data-storing nucleic acids are pooled with other nucleic acids that do not contain data of interest to the consumer.

One embodiment of the invention is related to a method for preparing a target nucleic acid sequence for analysis comprising, generating a set of barcodes comprising nucleic acids; affixing the barcodes to the target nucleic acid sequence to be analyzed; and combining or pooling the barcoded target nucleic acid sequence to be analyzed with a control or decoy nucleic acid sequence comprising a barcode.

One embodiment of the invention is related to a method for anonymizing a target nucleic acid sequence, the method comprising generating a set of barcodes comprising nucleic acids; affixing the barcodes to the target nucleic acid sequence; and combining or pooling the barcoded target nucleic acid sequence with a control or decoy nucleic acid sequence comprising a barcode, wherein the combination of the barcoded target nucleic acid sequence with the control or decoy nucleic acid sequence anonymizes the target nucleic acid sequence.

In some embodiments, a random amount of barcodes and/or non-barcoded target nucleic acids, and/or random amount of barcoded and/or non-barcoded decoy nucleic acids are pooled for sequencing. In these embodiments, randomness of the amounts that are to be pooled can be determined by a randomizing agent, such as a coin, set of dice, or a computer program designed by those skilled in the art. In these embodiments, the amount of randomness and/or method by which random amounts are determined are designed by those skilled in the art to ensure that the amount of privacy required by the consumer is achieved by the pooling.

In some embodiments, randomness is expected to occur due to the unpredictable nature of molecular biology methods. For one example, when nucleic acids are amplified using polymerase chain reaction, the exact number of copies of the nucleic acids targeted is unknown (but can be predicted within an error of margin). For another example, when a quantity of nucleic acids present within a solution is unknown, but again predicted with some margin of error, pooling that solution of nucleic acids with other nucleic acids results in a pool of nucleic acids in which the exact quantities of each oligonucleotide is not known with certainty. In some embodiments, randomness is obtained by pooling a group of nucleic acids and removing a subset of that pool, resulting in a random selection from that pool. In some embodiments, the randomness that occurs in molecular biology methods is estimated to predict how that randomness will impact the privacy and/or concealment used in the invention.

BRIEF DESCRIPTION OF DRAWINGS

FIGS. 1A-1C depict a work flow diagram for the barcoding (FIG. 1A) and pooling of nucleic acids (FIG. 1B), so that their information is concealed to individuals that do not have access to the table of barcodes (FIG. 1C), as described herein.

FIG. 3 depicts a description of the large number of potential barcodes that are possible using nucleic acids, as described herein.

DETAILED DESCRIPTION OF THE INVENTION

Figure 2:
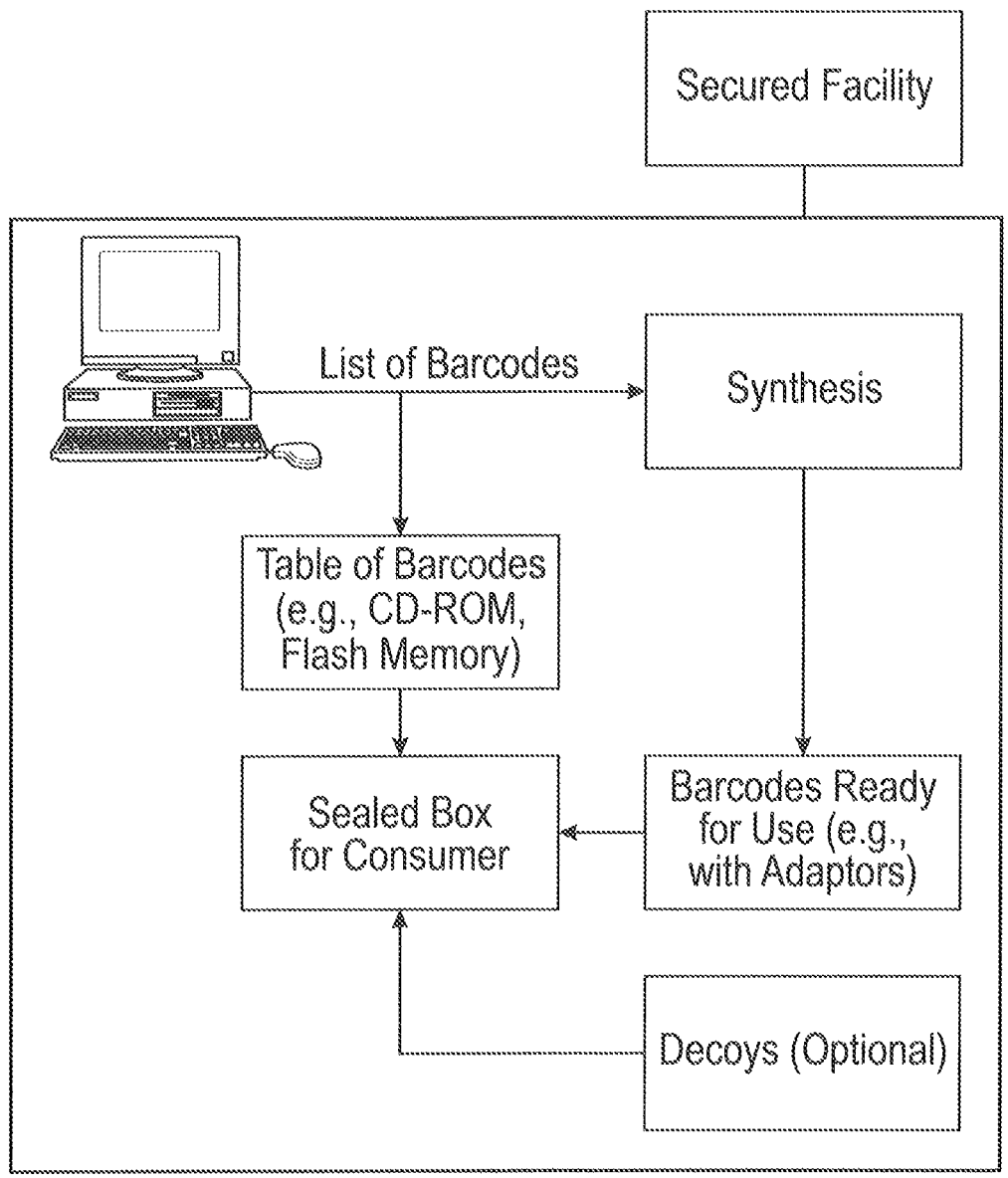
FIG. 2 depicts a work flow diagram for the secure generation of barcodes and any relevant materials used to affix these barcodes to nucleic acids or conceal nucleic acids after they have been barcoded, as described herein.

As used herein, the term "conceal" means to hide information, specifically in regard to information contained in nucleic acids. Concealment, the act of concealing information, can be achieved by various methods, each concealing different information present in nucleic acids. These include but are not limited to: reducing the ability to detect the presence of nucleic acids known to be derived from specific sources, reducing the ability to determine the traits present in the sources of nucleic acids, reducing the ability to determine which nucleic acids are derived from which sources, reducing the ability to obtain any data being stored in nucleic acids, reducing the ability to determine the types of sources from which nucleic acids were derived.

As used herein, the term "target nucleic acid" refers to nucleic acid oligonucleotides intended for analysis, such as sequence analysis.

As used herein, the term "decoy nucleic acid" refers to any nucleic acid oligonucleotide that is pooled with target nucleic acids to aid in the concealment of the target nucleic acids. These decoy nucleic acids may contain or be composed of target nucleic acids from various sources. That is, target nucleic acids from one source can be concealed within a pool of target nucleic acids from other sources, resulting in target nucleic acids that act as decoy nucleic acids for other target nucleic acids.

As used herein, the term "anonymize" refers to the reduction in the ability for target nucleic acids to be linked in any way to an individual, a family, an ethnicity, or any other named entity or group.

As used herein, the term "obfuscate" refers to the action of obscuring the purpose and/or situation and/or reason for which a target nucleic acid is being analyzed.

As used herein, the term "conceal" encompasses the terms "anonymize" and "obfuscate" and the use of the term conceal can mean to conceal and/or anonymize and/or obfuscate.

As used herein, the term "barcode" refers to an oligonucleotide that is used as an identifier for a target nucleic acid molecule.

In some embodiments, the technology described herein relates to the preparation of nucleic acids. In some embodiments, the methods described herein conceal information present in nucleic acids prior to their analysis (e.g. sequencing). In some embodiments, the methods described herein relate to enrichment of nucleic acids.

Nucleic acids can contain information used to identify the source of the nucleic acids. When their source is a person, any information about that person that is already known by a potential adversary helps to identify that person. This can be, for example, a rare mutation that is known to occur in individuals with a specific last name, from a specific region of the world, from a specific ethnicity, or any other characteristic of a person that is known to be associated with such nucleic acids variants. If nucleic acids variants can be used to determine characteristics of their source (e.g. that their source has red hair), then that information can be used to help identify that source. Anonymization is the reduction in information that can be used to identify a source.

Many individuals are combinations of different ethnicities; their ancestors originated from different places in the world. Consequently, their genetic makeup reflects these different ethnicities. The DNA inherited from the paternal lineage may be from a different ethnicity or ethnicities than the DNA originating from the maternal lineage.

By observing the ethnic composition of nucleic acids, the individual from which those nucleic acids originated may be identified. By combining other identifying information, such as hair color, body type or any other heritable trait, the source of nucleic acids may be even easier to determine. As disclosed herein, barcoding and pooling breaks up this information, such that individual pieces of information about the source of the nucleic acids are not grouped together as originating from an individual source. The types of barcoded nucleic acids that are pooled may originate from various ethnicities, with individuals with various heritable traits, such that an adversary with access to the sequence data would be unable to determine whether any specific individual has nucleic acids present in the pool. The barcoded pool consists of a collection of nucleic acids that contain variants from multiple sources, and determining the identity of any of these sources is hindered without the table linking barcodes to their sources.

To conceal information contained within nucleic acids, the technology described herein utilizes the following steps: (a) the secure generation of barcodes, and other requisite material to be used in the technology; (b) the affixing of barcodes to target nucleic acids (FIG. 1A); and (c) the pooling of barcoded target nucleic acids with other nucleic acids (FIG. 1B).

In some embodiments, the secure generation of materials to be used in this technology can occur in a secure facility (FIG. 2). In some embodiments, this facility does not require any communication outside of the facility. In some embodiments, materials are generated by machines, such as robots, and may not require any direct human involvement. In some embodiments, humans are involved in some steps of the process of material generation. To ensure security, if humans are involved, they must be screened prior to entering the facility to prevent them from using any recording device within the facility (e.g. camera) that may compromise information found within.

In some embodiments, to prevent any communication outside of the facility, there are no means of electronic communication between inside and outside of the facility. For example, there are no cables entering/exiting the facility that can be used for communication, such as but not limited to copper telephone lines or fiberoptic cable lines. To prevent electromagnetic signals from entering/exiting the facility, methods for blocking electromagnetic signals are employed, such as the use of a faraday cage surrounding the facility, or the jamming of electromagnetic communication by other means. In some embodiments, the area surrounding the facility is monitored for communication, with visual and auditory monitoring. In some embodiments, this monitoring includes the monitoring of electromagnetic signals to detect possible espionage. In some embodiments, all computer systems within the facility are "air-gapped" and all individuals entering/leaving the facility are monitored for unauthorized communication.

In some embodiments, within the facility a computer generates a set of random nucleic acids sequences to be used as barcodes. These barcode sequences would be generated in such a way as to prevent any prediction about the barcode sequences in the set using any information from that set, so that the set of barcodes is unique and also each barcode is generated to be a unique barcode that is otherwise entirely independent from other barcodes in the set. In some embodiments, these sequences are sent along a wire to a machine that produces the barcodes from nucleic acids, using a wire that has electromagnetic shielding so that information does not emanate from the wire. In some embodiments, the set of barcode sequences is generated by a computer that is incorporated into the machine that is used to generate the barcodes. In some embodiments, these barcodes are generated along with any materials linked to the barcodes that serves to aid in the affixing of barcodes to other nucleic acids. These materials include, but are not limited to, adapters, indexes or any other chemicals or molecules used in the next steps in the technology.

A large number of barcodes are possible using nucleic acids. Traditionally, four different types of nucleic acid bases are used in biotechnology; adenine, cytosine, thymine and guanine. In some embodiments, the technology herein can use any non-traditional nucleotide bases (e.g. 5-methylcytosine). In the technology described herein, the numerous barcodes that can be generated using only four nucleotide bases is discussed (FIG. 3), with the understanding that even more types of barcodes are possible if non-traditional nucleotide bases are utilized.

With four nucleotide bases, there are $4^n$ possible combinations of these nucleotides, where "n" is the length of the oligonucleotides in the barcodes. For example, if the barcode is of length four (n=4), there are $4^4$=256 possible different barcode sequences. If the length of the barcodes is allowed to vary, such that some barcodes are of a different length than others, then there are even more possible barcode sequences. For example, if there are barcodes of length 1, 2, 3, or 4, then there are $4^4+4^3+4^2+4^1$=340 possible sequences.

As the length of the barcodes increases, there quickly becomes a large number of possible barcodes. For example, if barcodes are of length eight, and only eight nucleic acids in length, there are 65,536 possible combinations. Lengthening barcodes to twenty, and only twenty nucleic acids in length, allows over one trillion different combinations. Not all barcode sequences may be ideal to use in some embodiments of this technology, and some barcodes can be excluded from use. Nevertheless, a large number of barcodes are possible, even after some are excluded.

In some embodiments, to determine which barcode sequences are ideal for a potential analysis, a computer program is used to examine the possible barcode sequences and compare them to other nucleotide sequences with which they may interact prior to or during analyses. The examination of possible barcode sequences can include, but is not limited to: prediction of their secondary structure (e.g. estimation of their ability to form the G-quadruplex DNA or RNA structure), examination for homopolymers runs, examination for homopurine/homopyrimadine regions, examination for hairpin-loop forming ability, or any other property of the sequence that may interfere with analyses and/or preparation for analyses. Comparison between possible barcodes and other sequences can include, but is not limited to: comparing barcodes for complementarity to other barcodes, comparing barcodes for ability to form alternative structures with other barcodes (such as triplex or quadruplex DNA formations), comparing the possible barcodes with potential target nucleic acids to avoid complementarity, or comparing the possible barcodes with any other sequences it may encounter during preparation or during analyses. In these embodiments, sequences that are not determined to be ideal for use are removed from the total set of possible barcode sequences, and those remaining are then randomly divided into subsets and manufactured.

In some embodiments, each subset contains a unique set of barcodes, while in other embodiments there are some barcodes present in different subsets that share identical sequences. Allowing some barcodes to be non-unique within a subset of barcodes, and/or allowing some barcodes to be non-unique between subsets of barcodes can aid concealment, depending on the analyses that may occur to target nucleic acids. In some embodiments, prior to barcode generation, a computer program can be used to determine whether non-uniqueness of barcodes is advisable for a proposed analysis. This computer program, generated by those skilled in the art, can also be used to determine whether all of the molecules to be analyzed require barcoding, or whether instead the analyses can allow some overlap of barcode sequences between different subsets and/or within a subset.

Figure 4:
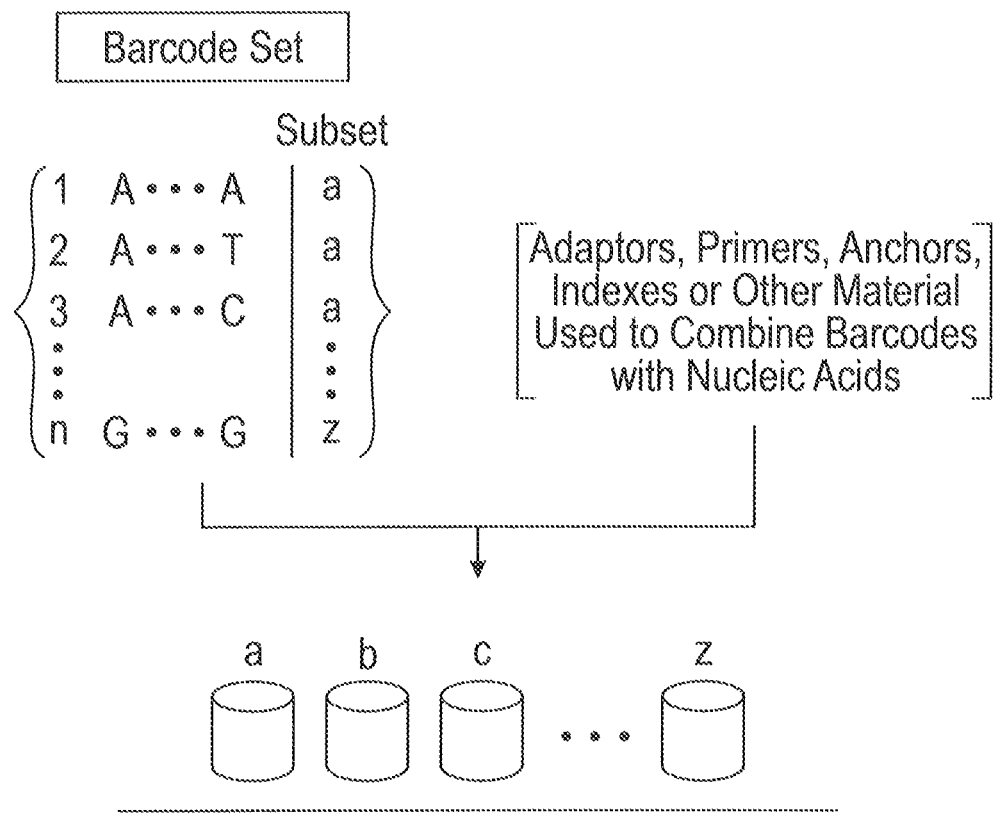
FIG. 4 depicts a work flow diagram for the generation of subsets of barcodes that are then placed separately in containers, with a table of barcodes that can be used to determine which barcodes are found in which containers, as described herein.

In some embodiments, the barcodes are generated in random subsets, such that these subsets of barcodes, and their relevant linked chemicals, are packaged separately from other subsets of barcodes (FIG. 4). In some embodiments, the barcodes are packaged in subsets without any relevant chemicals linked to them (i.e. they are packed as barcodes only). This packaging includes any requisite liquids or other chemicals used to stabilize or transport the chemicals within the package. In some embodiments, the subsets of barcodes are packaged together on a micro-well plate, such as a 96- or 384-well plate. In some embodiments, the tables of barcodes present in each subset are generated and printed out on paper. In some embodiments, the tables of barcodes present in each subset are transferred to an external data storage device, such as CD-ROM, DVD-ROM, or flash memory drive.

In some embodiments, the generation of barcodes includes some randomness in the exact sequence of the barcodes generated. In some embodiments, the randomness found in the barcode sequences is a consequence of the technology used to manufacture the barcodes. In some embodiments, the randomness induced into the construction of barcode oligonucleotides is added by a randomizing agent, such as a computer or other process that randomly directs the generation of the barcode oligonucleotides. For example, a barcode could be randomly generated as:

TACGCGAGATA<u>C</u> (SEQ ID NO: 1)
or
TACGCGAGATA<u>A</u> (SEQ ID NO: 2)
or
TACGCGAGATA<u>T</u> (SEQ ID NO: 3)
or
TACGCGAGATA<u>G</u> (SEQ ID NO: 4)

(in each of these examples, the last nucleotide in the sequence can take one of four nucleotide bases). This randomization may cause some barcodes in some subsets to be identical to barcodes in other subsets. In some embodiments, the random barcode sequence is perfectly recorded before, after or during the manufacture process, while in other embodiments, there is uncertainty about the exact barcode sequences present in each subset. Imperfect information about the exact barcode sequences present in each subset can provide additional security and/or reduce the cost of manufacturing, but, as a consequence can reduce certainty about the results from an analysis. This uncertainty can reduce the ability for a consumer and potential adversary to differentiate between target nucleic acids and decoys. In some embodiments, a cost-benefit analysis can be executed using a computer program designed by those skilled in the art to determine whether the benefits of random, potentially imperfectly known, barcode subsets are ideal for any specific uses of this technology.

In some embodiments, the subsets of barcodes and the table of the barcodes are sealed in a container, such that the seal cannot be resealed after it has been opened. In some embodiments, the containers with the barcodes and their related tables are sent by a trusted courier to customers. In other embodiments, these containers are shipped to a distribution center.

By securely generating barcodes in subsets, the consumer of this technology can chose which subsets of barcodes to use on their target nucleic acids, and which subsets they may possibly use on any decoy nucleic acids.

In some embodiments, the secure facility also produces decoy nucleic acids. These decoy nucleic acids are to be used in the future steps of the technology. In some embodiments, the nucleic acids sequences present in the decoys are shared with the consumer of this technology, using a medium such as paper or an electronic data format. In some embodiments, the exact nature of the decoys is not shared, and the set of decoy nucleic acids is shipped with only a general indication of the types of nucleic acids present. For example, a set of decoy nucleic acids may be a group of nucleic acids originating from a population, sub-group, ethnicity, species, subspecies, or strain of plant, breed of animal, strain of microbe, or a set of related nucleic acids from multiple species of plant/animal/microbe. In some embodiments these decoy nucleic acids are provided by a third party or by the consumer of the technology. In some embodiments, suggestions are made about which decoy nucleic acids to use. In some embodiments, the decoy nucleic acids are provided by both the consumer and the secured facility, and are combined by the consumer.

Providing decoy nucleic acids from a secure facility helps with the secure concealment of information contained within nucleic acids from the consumer, but because the barcodes are provided to the consumer, the consumer is able to securely generate barcoded decoy nucleic acids by themselves. The types of decoys that are optimal for concealment depend on the target nucleic acids, and the information that the consumer wishes to conceal. Preventing an adversary from having any prior knowledge about the decoy nucleic acids provides the greatest concealment, thus secret generation of decoy nucleic acids is ideal. The consumer may not have the capability to generate appropriate decoy nucleic acids, and in such instances providing decoy nucleic acids from a secure facility would be required.

Figure 5:
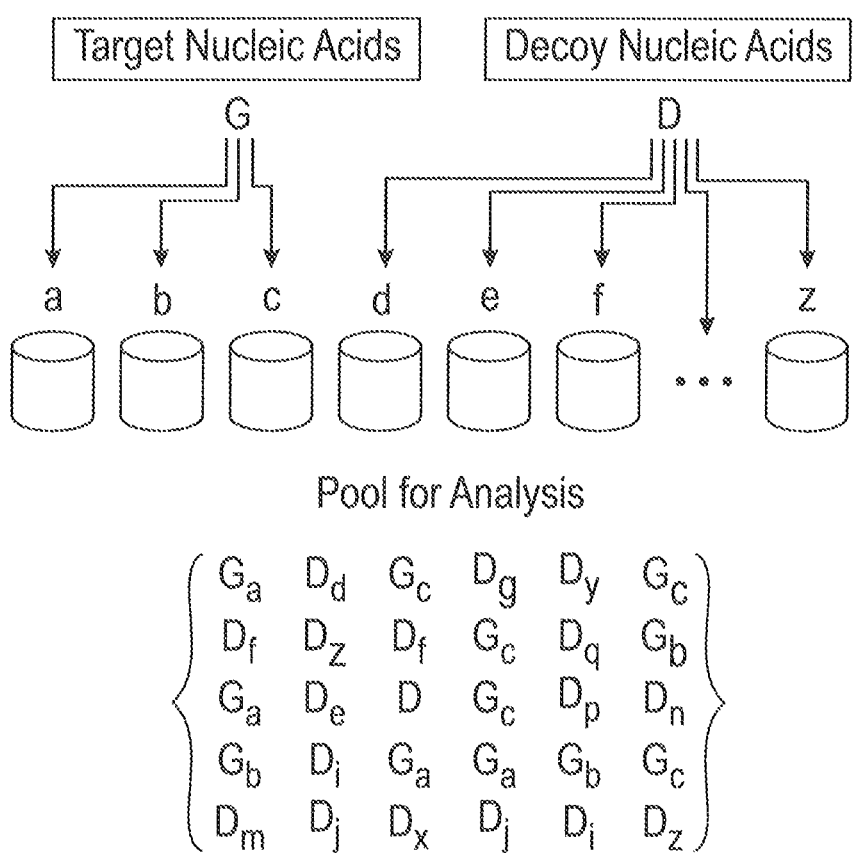
FIG. 5 depicts a workflow diagram for the use of subsets of barcodes to generate barcoded nucleic acids to be concealed with other barcoded nucleic acids by polling them together, as described herein.

In some embodiments, the barcoding of nucleic acids in this technology utilized the technology from U.S. patent publication numbers 2015/0211050 and 2015/0211061, which are incorporated herein by reference. In some embodiments, the use of this technology involves enrichment of target nucleic acids, with barcodes added during or before enrichment. The addition of barcodes before or during enrichment results in individual barcodes tagging multiple nucleic acids oligonucleotides that originated from the same oligonucleotide. In such embodiments, the decoy nucleic acids are also tagged with barcodes prior to or during enrichment so that, like the target nucleic acids, individual barcodes also tag multiple nucleic acids oligonucleotides in the decoy nucleic acids (FIG. 5).

In some embodiments, small barcodes are used, of length 1, length 2, length 3, length 4, length 5, length 6, length 7, or length 8 nucleic acids. In some embodiments small and large barcodes are used together, for example barcodes of length 8, length 9, length 10, length 11, length 12, length 13, length 14, length 15, length 16, length 17, length 18, length 19, length 20, length 21, length 22, length 23, length 24, length 25, length 26, length 27, length 28, length 29, and/or length 30, or longer. When barcodes of various lengths are used together and there is an enrichment step after the nucleic acids have been barcoded, the relative rates of enrichment of different oligonucleotides must be considered. For example, longer barcodes may require more time to be polymerized, and thus enriching nucleic acids tagged with these longer barcodes may result in fewer enriched nucleic acids molecules than nucleic acids tagged with shorter nucleic acids.

In some embodiments, barcodes and their indexes and adaptors will have different rates of polymerization, and thus rates of enrichment will differ between nucleic acids tagged with these different molecules. In some embodiments, rates of enrichment are varied due to modification of nucleic acid bases that alter rates of enrichment, due to alternative secondary structures that pause or otherwise slow the rate of polymerization, or due to the addition of other molecules to the barcodes to interfere with polymerase and vary the rates of enrichment. In these embodiments, the random effect that the barcodes, and their adapters and indexes, may have on rates of polymerization may be utilized to randomly vary the quantities of nucleic acids that have the different barcodes by altering the relative rates of enrichment that occurs during any enrichment steps in this technology.

In some embodiments, varying the rates of enrichment can be utilized to vary the quantity of the nucleic acids that have different barcodes, which may be used to further conceal the target nucleic acids. If some barcoded target nucleic acids are in different quantities than barcodes on the target nucleic acids, then it is more difficult to link these two nucleic acids as originating from the same source. For example, if an individual is to be sequenced for a genomic region (e.g. a gene), that individual likely has two distinct variants of this genomic region, one from each parent. If a similar quantity of each variant is present, then they may be attributed to a single source, but if the quantities of enriched barcoded variants is different for the two regions, then attributing these two regions to the same source becomes more difficult.

In some embodiments, barcodes are added with a ligation step, and in these embodiments, enrichment does not subsequently occur after the barcodes have been ligated. In some embodiments, there is an enrichment step prior to the ligation of barcodes. In some embodiments the enrichment step prior to the ligation of barcodes also adds barcodes.

Figure 6A:
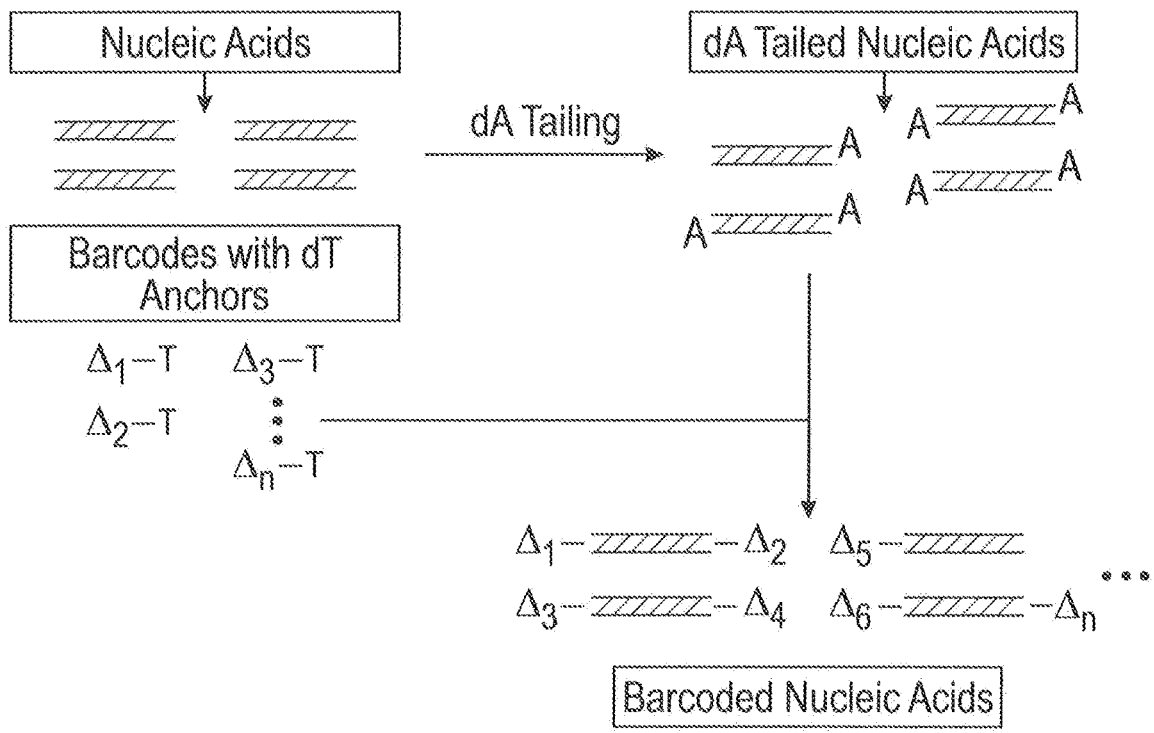
FIG. 6A and FIG. 6B depict workflow diagrams for affixing barcodes to nucleic acids using sticky-end ligation, as described herein.

In some embodiments, barcodes are ligated to target nucleic acids using sticky-end ligation. In some embodiments, the sticky-end ligation used is TA ligation (FIG. 6A), involving the addition of an adenosine nucleic acid to the target nucleic acids prior to ligation. In such embodiments, the barcodes are linked to an adapter molecule that contains an overhanging thymine nucleic acid to match the overhanging adenosine on the target nucleic acids.

Figure 6B:
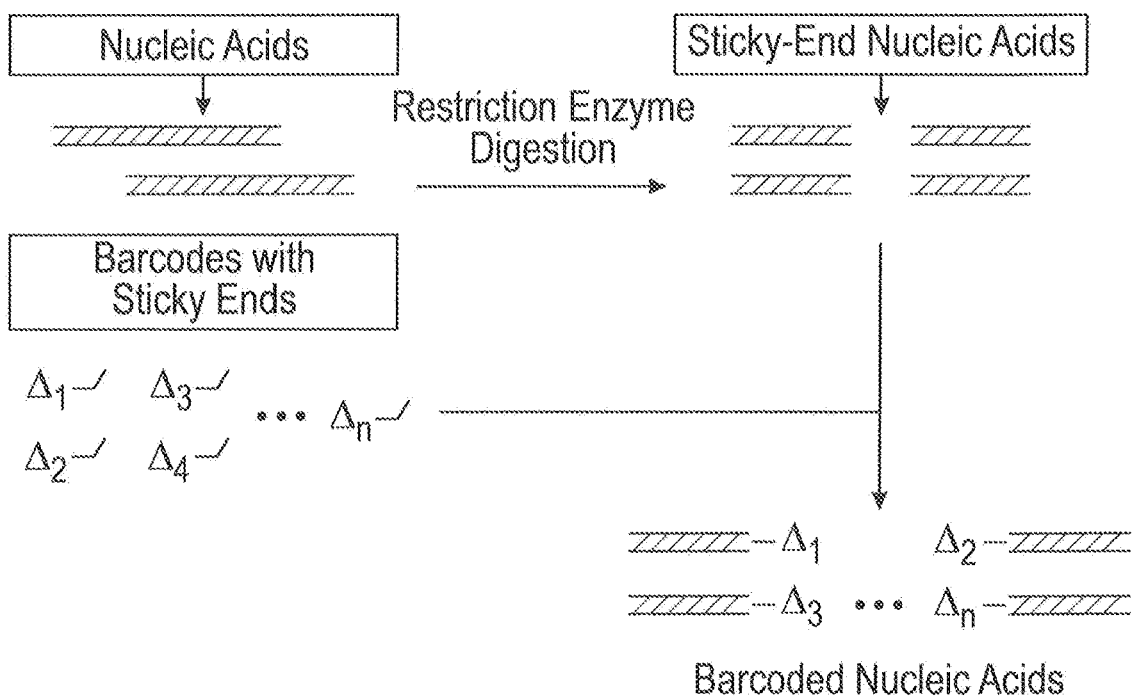

In some embodiments, a restriction enzyme is used on nucleic acids prior to ligation of barcodes (FIG. 6B). The cutting of nucleic acids with a restriction enzyme may serve multiple purposes, including but not limited to: breaking the nucleic acids into oligonucleotides of smaller size to facilitate requirements of the analyses (e.g. next-generation sequencing requires the input of oligonucleotides smaller than a certain length); separating regions of the nucleic acids from each other, so that possible variants present in the nucleic acids are not on the same molecule, further increasing concealment; Generating sticky ends on the nucleic acids to facilitate ligation with barcodes designed with adapters that correspond to the sticky-ends generated on the nucleic acids by the restriction enzyme digestion.

In some embodiments, barcodes are incorporated into steps used for the purpose of specific sequencing technology. Sequencing technology may require or benefit from the addition of molecules to nucleic acids prior to analysis. In some embodiments of this technology, the molecules added to nucleic acids prior to sequence analysis include the addition of barcodes designed for concealing the nucleic acids. For example, sequencing on Pacific Biosciences Real-Time sequencer benefits from the addition of a single stranded region to the nucleic acids to be sequenced (see U.S. patent publication number 2012/0196279, incorporated herein by reference). This single stranded region can contain barcode information, and in some embodiments of this technology, barcodes are added to this region to facilitate concealment of nucleic acids prior to analysis. In some embodiments, adding barcodes at this step is in addition to barcodes added at previous steps.

In some embodiments, barcodes are added to decoy nucleic acids by the consumer of this technology. In these embodiments, similar steps are taken with decoy nucleic acids as are taken with any target nucleic acids. In such embodiments, due to the ability of the consumer to choose which subsets of barcodes are added to which nucleic acids, only the consumer has knowledge of the barcodes that are present on the target nucleic acids and which are on the decoy nucleic acids (FIG. 5). In some embodiments, the decoy nucleic acids are barcoded and provided to the consumer by a secure facility. In these embodiments, the table of barcodes provide to the consumer would inform the consumer as to which barcodes they may add to their target nucleic acids. In some embodiments, the table of barcodes present on the decoy nucleic acids provided by the secure facility may not be disclosed to the consumer. In other embodiments the table of barcodes added to the decoy nucleic acids is provided to the consumer.

In some embodiments, some barcode sequences found on the target nucleic acids are identical to some barcode sequences found on the decoy nucleic acids. In such embodiments, knowledge of the barcodes present on the decoy nucleic acids is necessary, and the table of barcodes would be provided for the decoy nucleic acids provided by the secure facility. Overlap between the set of barcodes on the target nucleic acids and the decoy nucleic acids can provide further concealment about which nucleic acids are targets and which are decoys, as even the consumer would not have full information! In such embodiments, the consumer can still obtain useful information about the target nucleic acids as long as a sufficient number of unique barcodes are present on the target nucleic acids. In some embodiments, the number of unique barcodes required to obtain sufficient information about target nucleic acids is determined by the consumer. In some embodiments, advice is provided about how many barcodes can overlap between the target and decoy nucleic acids.

In some embodiments, not all target and/or decoy (control) nucleic acids receive a barcode. In some embodiments, some of the non-barcoded adapters, primers, or other material that would otherwise contain a barcode are generated without barcodes. In some embodiments, when barcodes are added after or without an amplification step, barcodes can be ligated to nucleic acids in such a way that not all nucleic acids receive a barcode (e.g. a limited amount of barcodes are added to nucleic acids such that not all nucleic acids receive a barcode). In some embodiments, a computer program generated by those skilled in the art can be used to determine whether analyses can provide sufficient information if not all of the target nucleic acids are barcoded.

In some embodiments, the randomness that is intrinsic to molecular biology procedures and techniques can be utilized to aid in concealment. In these embodiments, concealment can be aided by randomizing the barcoding of nucleotides prepared for analysis. In some embodiments, the proportion and/or number of nucleic acids that receive any barcodes is randomized. In some embodiments the number of nucleic acids that receive the same barcode is randomized. For example, if barcodes are added during or before an enrichment step, then the relative quantities of identical barcodes found in the total pool of nucleic acids would be affected by randomness in the molecular process by which the nucleic acids were amplified. In some embodiments, randomness in the number and/or proportion of barcodes that receive any barcode is utilized to aid in concealment. If the method used to affix barcodes to nucleic acids results in fewer than every nucleic acid receiving a barcode, then the specific nucleic acids that receive or do not receive a barcode can, in some embodiments, be random. In some embodiments, estimates of the distribution of quantities of various nucleic acids, and the effect that the randomization procedure has on concealment, can be predicted using a computer program generated by those skilled in the art. In some embodiments, computer programs used to estimate randomness can also direct how randomness is achieved using molecular genetics procedures.

The methods for pooling nucleic acids in this technology depend upon various factors, including but not limited to: the type of nucleic acids being targeted (e.g. the species, subspecies, or ethnicity of the target nucleic acids), the potential knowledge an adversary may have about the target nucleic acids, the type of information the consumer wishes to conceal, the accuracy of the technology used to analyze the nucleic acids, the availability of decoy nucleic acids to the consumer, the knowledge available about the target nucleic acids, the cost of sequence analyses, the funding available for analyses, or any other factor that affects the information the consumer and/or a potential adversary may have about the target nucleic acids and the decoy nucleic acids being used.

The methods provided herein provide various techniques for pooling nucleic acids for concealment. The use of pooling barcoded nucleic acids for concealment is not limited to the examples provided herein.

In some embodiments, simulations and/or computer programs capable of simulations are provided to the consumer to help them make decisions about pooling. In some embodiments, one or more measures of privacy, such as differential privacy (see U.S. Pat. No. 7,698,250, incorporated herein by reference) are used to determine the type of pooling necessary for a level of privacy chosen by the consumer. In some embodiments, suggestions are made to the consumer regarding methods of pooling.

In some embodiments, the pool of decoy nucleic acids consists partially or entirely of other target nucleic acids, i.e. target nucleic acids that are not identical to each other. By using target nucleic acids from one source as decoy nucleic acids for target nucleic acids from other sources, the relative cost of useful analyses is decreased. If some, or all, of the decoy nucleic acids that are used are not target nucleic acids of interest to the consumer, then pooling target nucleic acids with these decoys requires the analyses of uninteresting nucleic acids. As the cost of sequencing analyses continues to decrease, the addition of uninteresting decoy nucleic acids to the pool of nucleic acids for analysis will become relatively less expensive. However, in some embodiments of this technology, all of the nucleic acids pooled are of interest to the consumer (i.e. multiple target nucleic acids serve as decoys for each other), therefore this technology does not require inexpensive sequencing to be cost effective for the consumer. In some embodiments, the decisions about pooling are influenced by the cost of analyses and the budget the consumer has for analyses.

Pooling barcoded nucleic acids can conceal information about those nucleic acids. The information that is desired to be concealed determines the method of pooling. Examples of the types of information present in nucleic acids that can be concealed with this technology are provided herein. The use of this technology to conceal information is not limited to the examples provided herein.

As a prophetic example, assume the target nucleic acids originates from a person, and their target nucleic acids have been enriched for a gene that may confer disease risk (e.g. BRCA1 gene variant that predisposes one to breast/ovarian cancer.) Assume the target nucleic acids have been barcoded and combined with barcoded nucleic acids originating from the same gene from other individuals (the decoy pool). Assuming that the decoy pool consists of ethnically similar individuals, the composition of the entire pool is nearly identical to the decoy pool alone before the target was added. Therefore, any adversary would be challenged to determine if any individual is present in the pool, as the pool only changes slightly when an individual's nucleic acids are added to the pool. Therefore, information from nucleic acids that may be used to identify an individual in the pool is concealed with the use of unique molecular barcodes. An adversary can determine that the pool consists of many copies of a gene from multiple unknown individuals, but would be challenged to identify these individuals.

Anonymization of nucleic acids using a large pool of nucleic acids from a matching population requires that the entire pool be analyzed to obtain information about a single target. As discussed, when the pool of decoy nucleic acids consists of other target nucleic acids, all information provided from the analysis of the pool is of some use to the consumer. In some embodiments, the pool consists entirely of target nucleic acids that serve as decoys for each other. In some embodiments, the pool consists of decoy nucleic acids of no interest to the consumer, only acting to conceal the target nucleic acids. In some embodiments, the decoy pool is a combination of various sources, some of which are target nucleic acids of interest to the consumer, some of which is decoy nucleic acids of no interest to the consumer.

Genetic information about traits that may not necessarily help identify the source of nucleic acids may also be obtainable from analyses of nucleic acids (e.g. disease risk). In some embodiments, the technology described herein may also conceal that trait information. For some traits, a combination of nucleic acid variants is used to predict the traits. For example, an individual homozygous at a locus in their genome may be predisposed to a disease. Barcoding and pooling breaks up information from different parts of the target nucleic acids. For example, the allelic variants inherited from one parent are barcoded differently than the allelic variants from the other parent, so determining the genotypes that an individual inherited requires the use of the table of barcodes. Consequently, even pooling methods designed entirely for anonymization results in concealment of other information present in the nucleic acids.

However, some methods of pooling provide increased concealment about trait information. For another prophetic example, assume again that targets are being analyzed for mutation in a gene (e.g. again like BRCA1), and assume that their barcoded nucleic acids are pooled together to act as decoys for each other. Using this pool, an adversary may obtain trait information about the pool in general. For example, if many individuals in the pool are carrying BRCA1 variants that predispose them to cancer risk, then an adversary with access to the sequence analysis would be able to determine that the pool has a relatively higher risk of cancer than the general population. Decoy nucleic acids can be chosen for a pool such that trait information is concealed. Within the same prophetic example, decoy nucleic acids could be chosen so that the pool appears to have similar amounts of disease risk variants as the general population. In this scenario, the individuals from which the pool of sequenced nucleic acids was derived would be predicted to have traits present at rates comparable to rates already known to occur in the general population. Thus, the pool becomes uninformative about traits present in the pool. In some embodiments, nucleic acids are pooled to conceal the traits present in the pool by designing the pool to appear to contain traits at rates similar to a background population.

When decoy nucleic acids are chosen that do not originate from target nucleic acids, traits can become further concealed because the traits present in the pool can be more accurately controlled. In some embodiments, decoy nucleic acids are added to make the pool appear to have specific traits, concealing the traits of the sources of the target nucleic acids in the pool. In some embodiments, decoy nucleic acids with known traits (e.g. high cancer risk genetic variants) are added to the pool, making the pool enriched for nucleic acids variants with that trait. The overwhelming presence of nucleic acids with a predicted trait can conceal whether the target nucleic acids also have that trait. For a prophetic example, we take the same pool of target nucleic acids being analyzed for a trait (e.g. cancer risk using the BRCA gene from individuals) and we add a large amount of decoy nucleic acids with that trait. The pool now appears to contain many individuals with that trait, regardless of the traits of the sources of the target nucleic acids.

In some embodiments, target nucleic acids can a priori be believed to have specific traits due to other factors, such as traits measured in the source of the target nucleic acids, traits present in the family of the source of target nucleic acids, a pedigree analysis of the source of the target nucleic acids, ethnic background of the target nucleic acids, or any other information known about the source of the target nucleic acids. In some embodiments, target nucleic acids are pooled using this information.

In some embodiments, randomness is utilized to vary the quantities of nucleic acids from various sources that are added to the pool. In some embodiments, randomness occurs in the molecular genetics protocols used to prepare nucleic acids for analyses. For one example, the amplification of nucleic acids results in the production of a random quantity of nucleic acids. For another example of randomness in molecular biology techniques, the aliquoting of a liquid containing nucleic acids into a another liquid, that may or may not already contain nucleic acids, has limited precision. Thus, the exact quantity of a nucleic acid that gets aliquoted is random. Furthermore, when a nucleic acid is analyzed, the exact results of the analyses contain randomness in many ways, including but not limited to: randomness in the exact nucleic acid oligonucleotide that receives analysis, randomness in the quality of results of the analysis (e.g. random errors), and/or randomness in the quantity of results for a given nucleic acid oligonucleotide.

In some embodiments, the randomness intrinsic to molecular biology techniques is modified by the consumer. In some embodiments, the consumer modifies their lab techniques to increase the randomness of the quantities of nucleic acids in a pool. This randomness can include, but is not limited to: using lab techniques that are known to increase randomness (e.g. a pipetting technique that has a reduced precision in the quantity pipetted), using a nucleic acid amplification method that is known to have reduced precision in the quantities of nucleic acids that result from amplification (e.g. the use of a thermocycler that has limited precision in timing and/or temperature), and/or the use of reagents and chemicals that are known to introduce randomness (e.g. in the purification of nucleic acids, or in the amplification of nucleic acids). In some embodiments, the use of a randomizing agent (such as but not limited to a coin, dice, or computer) to further randomize the techniques used to prepare nucleic acids. The randomizing agent can randomize any step in the nucleic acid preparation and/or analyses to further randomize lab techniques to randomize the quantities of nucleic acids that are purified, isolated, amplified, and/or aliquoted to increase randomness in the quantities of nucleic acids in the resulting pool. Those skilled in the art can determine the bounds of the random quantities of materials that are allowed for any given technique or group of techniques to ensure that all of the randomly derived protocols are successful. For one prophetic example, the flips of a coin can be used to determine the quantities of nucleic acids that are added to a pool, with the minimum value allowable (driven be the randomizing agent, here a coin) determined by one skilled in the art to ensure that sufficient nucleic acids are present for a successful analysis.

In some embodiments, a computer program designed by those skilled in the art is used to determine how much randomness is ideal for a given application of this technology. In some embodiments, information theory is used to measure how much randomness may occur by pooling. In some embodiments, adversarial modeling is used to determine how much randomness is used in pooling. In some embodiments, estimates of the additional costs incurred by random pooling are used to determine how much randomness is used in pooling. Such costs can include, but are not limited to, costs incurred by randomly varying the quantities of nucleic acids through amplification and/or pipetting of random quantities of different nucleic acids, and costs incurred by the need to increase the total sequencing required to sufficiently analyze target nucleic acids. When nucleic acids are pooled randomly, there is a chance that some target nucleic acids will only occur at small quantities within the pool. When such a pool is then analyzed, these less common nucleic acids will subsequently receive fewer analyses than more common nucleic acids. Increasing the total analyses done on the pool can ensure that even the less common nucleic acids receive sufficient analyses. In some embodiments, the total quantity of analyses required for a given random pooling method are estimated by those skilled in the art.

Variation caused by randomness in the sequencing protocols can further aid in concealment. Sequencing analyses utilize a pool of nucleic acids to generate sequence data. These data are not provided equivalently to each nucleic acid in the pool. Sequencing results in some nucleic acid oligonucleotides generating one or more nucleic acid sequences in the data, while other nucleic acid oligonucleotides in the same pool generate no sequences in the data. Further, the sequence data generated by the sequencer does not provide equal quality sequence data results for all oligonucleotides that are sequenced. In some embodiments, a computer program designed by those skilled in the art would be used to estimate intrinsic randomness of an analysis, propose additional randomness that would introduce further random variation between different sample quantities, and/or estimate the privacy obtained by these methods. Similarly, a computer program can be used to estimate whether non-unique barcodes (between or within subsets of barcodes) can and/or should be used to provide increased security and/or limit the amount of barcodes used in the analysis.

In some embodiments, anonymization is of limited interest to the consumer and concealment of other information in the target nucleic acids is prioritized. For example, if an adversary has access to the sequence analysis results and also knows the sources of the nucleic acids being analyzed. A method for "family pooling" can be employed to conceal the nucleic acids of the offspring of the family. The nucleic acids of offspring are composed primarily of nucleic acids originating from each parent. If a large pool of nucleic acids consists of nucleic acids from each parent, then a small amount of nucleic acids from the offspring can be added to the pool with only minor alterations to the pool. The nucleic acids from offspring can thus be conveniently hidden in a pool of nucleic acids from its parents. In some embodiments of this technology, family pooling is employed to conceal nucleic acids of offspring. In some embodiments of family pooling, varying amounts of nucleic acids originating from each parent are used. In some embodiments, nucleic acids from parents and offspring are enriched, with barcodes added during enrichment. In some embodiments, some nucleic acids are enriched more than others by varying the rate at which nucleic acids with different barcodes are enriched. In some embodiments, variation of target nucleic acids or decoy nucleic acids occurs by varying the rates of enrichment using other means, such as varying the number of cycles of polymerization that occur during enrichment for example. In some embodiments, various quantities of different nucleic acids are present to the pool by varying the amount of different nucleic acids that are added.

By randomly varying the relative quantities of variants in a pool, the relative frequencies of different variants are altered. Offspring nucleic acids can then be further concealed in a pool of parental nucleic acids, because otherwise the relative rates of variants present in a pool may help indicate which variants where inherited by the offspring.

A similar method can be used to conceal nucleic acids from offspring in a breeding program. For example, diploid organisms can be hybridized to optimize a desired trait or traits, and nucleic acid analyses can help determine the traits of the offspring before that trait manifests. For example, milk production in cattle can be estimated in calves using nucleic acid analyses, crop yield can be estimated in the nucleic acids from young plants, or nucleic acid analyses can help predict any other trait that requires maturation of the offspring before the trait is fully manifested. In some embodiments, this "pedigree pooling" can be used to conceal information about offspring in breeding programs by barcoding and pooling the offspring in the breeding program. In some embodiments, barcoded nucleic acids originating from parents or other relatives of the offspring are pooled with barcoded nucleic acids from the offspring to aid concealment. In some embodiments, the offspring nucleic acids alone are barcoded and pooled together to serve as decoys for each other. In some embodiments, randomness is utilized in the pooling. Similar to the application of randomness described previously, a computer program can be used to estimate intrinsic randomness in the process, and offer methods for further randomizing the barcoding and/or pooling to achieve the desired security.

In embodiments employing "pedigree pooling" the adversary would be able to determine the mixture of the pool as originating from various breeds of plant or animal, but would be challenged to determine how the breeds have been mixed in the pedigree, or whether they were pure-breeds that had their nucleic acids mixed together in a pool. In some embodiments, pooling is designed to conceal the types of breeds and or hybrid present in a breeding program by pooling nucleic acids originating from large numbers of diverse offspring and/or their relatives.

Breeders may be breeding lineages of hybrids that have been selected for specific heritable traits, thus resulting in specific nucleic acids being present in those hybrids. Therefore, those hybrids would contain specific quantities of different variants from different lineages, and nucleic acid analyses of these hybrids might reveal information about the breeding program and traits present in the breeds. In some embodiments, nucleic acids originating from original breeds are mixed with the nucleic acids originating from the hybrids to alter the relative frequencies of different variants, further concealing the traits present in the breeds of interest and obfuscating the breeding program.

In some embodiments, nucleic acids are being used as a data storage medium and this technology is employed to conceal the data being stored in the nucleic acids. In some embodiments, the barcoding of these data-storage nucleic acids is sufficient to conceal information in those nucleic acids, and additional barcoded nucleic acids are not added to the pool of data containing nucleic acids (i.e. parts of the target nucleic acids can act as decoys for the other parts). In some embodiments, barcoded nucleic acids that contain data are pooled with barcoded nucleic acids that do not contain data. In some embodiments, barcoded nucleic acids that contain data are pooled with barcoded nucleic acids that originated from an organism, concealing the data-containing nucleic acids within a pool of the organism's nucleic acids.

All of the documents cited herein are incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. A method for concealing nucleic acids, the method comprising: (a) generating a set of barcode oligonucleotides;
   (b) affixing a subset of barcode oligonucleotides from the set of step (a) to a 5'- or 3'-end of target nucleic acids to create a set of barcoded target nucleic acids;
   (c) concealing the set of barcoded target nucleic acids by pooling the set of barcoded target nucleic acids with one or more barcoded decoy nucleic acids to create a mixture of barcoded target nucleic acids and barcoded decoy nucleic acids, where the barcoded decoy nucleic acids contain a unique subset of barcode oligonucleotides different from the subset affixed to the target nucleic acids;
   (d) preparing a table listing the identity and sequence(s) of the subset of barcode oligonucleotides affixed to the target nucleic acids and the identity and sequences of the barcode oligonucleotides of the barcoded decoy nucleic acids; and

```
SEQUENCE LISTING

<160> NUMBER OF SEQ ID NOS: 4

<210> SEQ ID NO 1
<211> LENGTH: 12
<212> TYPE: DNA
<213> ORGANISM: Artificial Sequence
<220> FEATURE:
<223> OTHER INFORMATION: Synthetic

<400> SEQUENCE: 1
tacgcgagat ac                                                             12

<210> SEQ ID NO 2
<211> LENGTH: 12
<212> TYPE: DNA
<213> ORGANISM: Artificial Sequence
<220> FEATURE:
<223> OTHER INFORMATION: Synthetic

<400> SEQUENCE: 2
tacgcgagat aa                                                             12

<210> SEQ ID NO 3
<211> LENGTH: 12
<212> TYPE: DNA
<213> ORGANISM: Artificial Sequence
<220> FEATURE:
<223> OTHER INFORMATION: Synthetic

<400> SEQUENCE: 3
tacgcgagat at                                                             12

<210> SEQ ID NO 4
<211> LENGTH: 12
<212> TYPE: DNA
<213> ORGANISM: Artificial Sequence
<220> FEATURE:
<223> OTHER INFORMATION: Synthetic

<400> SEQUENCE: 4
tacgcgagat ag                                                             12
```

(e) securing the mixture of barcoded target nucleic acids and the table by sealing both in a container that indicates when a seal of the container is broken.

2. The method of claim 1, wherein the subset of barcode oligonucleotides affixed to the target nucleic acids have different sequences.

3. The method of claim 1, wherein the subset of barcode oligonucleotides affixed to the target nucleic acids have identical sequences.

4. The method of claim 1, wherein the set of barcode oligonucleotides are randomly generated.

5. The method of claim 1, wherein the subset of barcode oligonucleotides are affixed to the target nucleic acids of step (b) before or during an enrichment step.

6. The method of claim 5, wherein the subset of barcode oligonucleotides affixed before or during the enrichment step alter the relative amounts of target nucleic acids with different barcode oligonucleotides.

7. The method of claim 5, wherein the rates of enrichment for different target nucleic acids are randomly varied.

8. The method of claim 1, wherein the subset of barcode oligonucleotides are affixed to the target nucleic acids using sticky-end ligation.

9. The method of claim 8, wherein the subset of barcode oligonucleotides are affixed to the target nucleic acids using TA ligation.

10. The method of claim 8, wherein the target nucleic acids are digested with restriction enzymes prior to step (b) to produce target nucleic acids with sticky-ends.

11. The method of claim 10, wherein the set of barcode oligonucleotides contain sticky-ends that correspond to the sticky-ends generated by the restriction enzymes, and these sticky-ends are used to ligate the barcode oligonucleotides with sticky-ends to target nucleic acids with sticky-ends.

12. The method of claim 10, wherein sonication is used to separate variants in the target nucleic acids prior to step (b).

13. The method of claim 8, wherein the digestion with restriction enzymes reduces the size of the set of barcode oligonucleotides.

14. The method of claim 8, wherein the digestion with restriction enzymes separates variants in the target nucleic acids from each other.

15. The method of claim 1, wherein the subset of barcode oligonucleotides affixed to the target nucleic acids have nucleotide sequences selected from any one of SEQ ID NO: 1-4.

* * * * *